United States Patent
Ran et al.

(10) Patent No.: US 9,738,623 B2
(45) Date of Patent: *Aug. 22, 2017

(54) CURCUMIN ANALOGS

(71) Applicant: The General Hospital Corporation, Boston, MA (US)

(72) Inventors: Chongzhao Ran, Winchester, MA (US); Xueli Zhang, Malden, MA (US); Anna Moore, Stoneham, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/419,985

(22) PCT Filed: Aug. 6, 2013

(86) PCT No.: PCT/US2013/053833
§ 371 (c)(1),
(2) Date: Feb. 6, 2015

(87) PCT Pub. No.: WO2014/025808
PCT Pub. Date: Feb. 13, 2014

(65) Prior Publication Data
US 2015/0158841 A1    Jun. 11, 2015

Related U.S. Application Data

(60) Provisional application No. 61/742,264, filed on Aug. 6, 2012.

(51) Int. Cl.
| | |
|---|---|
| *C07D 403/02* | (2006.01) |
| *C07D 407/02* | (2006.01) |
| *C07D 405/14* | (2006.01) |
| *C07D 401/06* | (2006.01) |
| *C07C 225/16* | (2006.01) |
| *C07D 213/74* | (2006.01) |
| *C07D 213/89* | (2006.01) |
| *C07D 231/12* | (2006.01) |
| *C07D 233/60* | (2006.01) |
| *C07D 471/06* | (2006.01) |
| *C07D 277/64* | (2006.01) |
| *C07F 5/02* | (2006.01) |
| *C07C 49/248* | (2006.01) |
| *C07C 49/252* | (2006.01) |
| *C07C 225/22* | (2006.01) |

(52) U.S. Cl.
CPC .......... *C07D 401/06* (2013.01); *C07C 49/248* (2013.01); *C07C 49/252* (2013.01); *C07C 225/16* (2013.01); *C07C 225/22* (2013.01); *C07D 213/74* (2013.01); *C07D 213/89* (2013.01); *C07D 231/12* (2013.01); *C07D 233/60* (2013.01); *C07D 277/64* (2013.01); *C07D 405/14* (2013.01); *C07D 471/06* (2013.01); *C07F 5/022* (2013.01)

(58) Field of Classification Search
CPC .. C07D 405/14; C07D 213/74; C07D 401/06; C07D 233/60; C07D 471/06
USPC ........................ 546/275; 548/313.7; 564/443
See application file for complete search history.

(56) References Cited

U.S. PATENT DOCUMENTS

| | | | |
|---|---|---|---|
| 4,522,811 A | 6/1985 | Eppstein et al. | |
| 6,468,798 B1 | 10/2002 | Debs et al. | |
| 6,471,996 B1 | 10/2002 | Sokoll et al. | |
| 6,472,375 B1 | 10/2002 | Hoon et al. | |
| 6,503,713 B1 | 1/2003 | Rana | |
| 6,881,584 B1 | 4/2005 | Lenhard et al. | |
| 6,983,753 B1 | 1/2006 | Lenhard et al. | |
| 7,277,744 B2 | 10/2007 | Schaefer et al. | |
| 2007/0060644 A1 | 3/2007 | Vander Jagt et al. | |
| 2008/0033055 A1 | 2/2008 | Miller et al. | |
| 2008/0146660 A1 | 6/2008 | Lee et al. | |
| 2008/0161391 A1 | 7/2008 | Lee et al. | |
| 2010/0216859 A1 | 8/2010 | Chen | |
| 2011/0208064 A1 | 8/2011 | Chongzhao et al. | |
| 2014/0275969 A1 | 9/2014 | Lau | |
| 2015/0087937 A1 | 3/2015 | Chongzhao et al. | |

FOREIGN PATENT DOCUMENTS

| | | | |
|---|---|---|---|
| CN | 102603782 | * | 7/2012 |
| WO | WO 2010/017094 | | 2/2010 |
| WO | 2010/068935 | | 6/2010 |
| WO | 2010/074971 | | 7/2010 |
| WO | 2010/132815 | | 11/2010 |
| WO | 2011/014648 | | 2/2011 |
| WO | WO 2011014648 | | 2/2011 |

OTHER PUBLICATIONS

International Preliminary Report on Patentability in International Application No. PCT/US2013/053833, issued Feb. 10, 2015, 7 pages.
Berge et al., "Pharmaceutical Salts," J Pharmaceutical Sci, 66(1):1-19 (1977).
Hamajima et al., "Intranasal administration of HIV-DNA vaccine formulated with a polymer, carboxymethylcellulose, augments mucosal antibody production and cell-mediated immune response," Clin Immunol Immunopathol. Aug. 1998;88(2):205-10.
Popic et al., "An Improved Synthesis of 2-diazo-1,3-diketones," Synthesis, 1991, 3:195-8.
Ran and Moore, "Spectral unmixing imaging of wavelength-responsive fluorescent probes: an application for the real-time report of amyloid Beta species in Alzheimer's disease," Mol Imaging Biol. Jun. 2012;14(3):293-300.

(Continued)

*Primary Examiner* — Rita Desai
(74) *Attorney, Agent, or Firm* — Fish & Richardson P.C.

(57) ABSTRACT

Provided herein are curcumin analogues that are able to interact with amyloid β (Aβ) and to attenuate the copper-induced crosslinking of Aβ. Also provided herein are methods of using the compounds in the treatment of Alzheimer's Disease or a related disorder.

22 Claims, 11 Drawing Sheets

(56) References Cited

OTHER PUBLICATIONS

Ran et al., "Design, synthesis, and testing of difluoroboron-derivatized curcumins as near-infrared probes for in vivo detection of amyloid-beta deposits," J Am Chem Soc. Oct. 28, 2009;131(42):15257-61 (Author Manuscript).
Ran et al., "Non-conjugated small molecule FRET for differentiating monomers from higher molecular weight amyloid beta species," PLoS One. Apr. 29, 2011;6(4):e19362, 6 pages.
Ravin, "Preformulation," Remington's Pharmaceutical Sciences, 17th ed., Mack Publishing Company, Easton, Pa., 1985, pp. 1409-1418.
International Search Report and Written Opinion mailed Dec. 5, 2013 in international application No. PCT/US2013/053833, 10 pgs.
Aleo et al., "Mechanism and Implications of Brown Adipose Tissue Proliferation in Rats and Monkeys Treated with the Thiazolidinedione Darglitazone, a Potent Peroxisome Proliferator-Activated Receptor-γ Agonist," The Journal of Pharmacology and Experimental Therapeutics, 2003, 305:1173-1182.
Baranova et al., "CD36 Is a Novel Serum Amyloid A (SAA) Receptor Mediating SAA Binding and SAA-induced Signaling in Human and Rodent Cells," J Biol Chem, Mar. 2010, 285(11):8492-8506.
Bartelt et al., "Brown adipose tissue activity controls triglyceride clearance," Nature Medicine, Feb. 2011, 17(2): 200-205.
Basu, "Functional imaging of brown adipose tissue with PET: can this provide new insights into the pathophysiology of obesity and thereby direct antiobesity strategies?," Nuclear Medicine Communications, 2008, 29(11): 931-933.
Boss and Farmer, "Recruitment of brown adipose tissue as a therapy for obesity-associated diseases," Frontiers in Endocrinology, Feb. 2012, 3: 118-123.
Bostrom et al., "A PGC1α-dependent myokine that drives browning of white fat and thermogenesis," Nature, 481: 463-468.
Burcelin et al., "Changes in uncoupling protein and GLUT4 glucose transporter expressions in interscapular brown adipose tissue of diabetic rats: relative roles of hyperglycaemia and hypoinsulinaemia," The Biochemical Journal, 1993, 291: 109-113.
Cannon and Nedergaard, "Brown adipose tissue: function and physiological significance," Physiological Reviews, Jan. 2004, 84: 277-359.
Chen et al., "Anatomical and Functional Assessment of Brown Adipose Tissue by Magnetic Resonance Imaging. Obesity," Jul. 2012, 20(7): 1519-1526.
Coburn et al., "Role of CD36 in membrane transport and utilization of long-chain fatty acids by different tissues," J Mol Neurosci., 2001, 16(2-3):117-121.
Cypess et al., "Identification and importance of brown adipose tissue in adult humans," The New England Journal of Medicine, Apr. 2009,360: 1509-1517.
Czarnik, "Encoding methods for combinatorial chemistry," Curr. Opin. Chem. Bio., Jun. 1997, 1:60-6.
Demers et al., "Identification of the growth hormone-releasing peptide binding site in CD36: a photoaffinity cross-linking study," Biochem. J., 2004, 382:417-424.
Farmer, "Molecular determinants of brown adipocyte formation and Function," Genes & Development, 2008, 22: 1269-1275.
Garcia-Alloza et al., "Curcumin labels amyloid pathology in vivo, disrupts existing plaques, and partially restores distorted neurites in an Alzheimer mouse model," J. Neurochem., Aug. 2007, 102: 1095-1104.
Greenwalt et al., "Heart CD36 Expression Is Increased in Murine Models of Diabetes and in Mice Fed a High Fat Diet," J Clin Invest., 1995, 96(3):1382-1388.
Gunawardana and Piston, "Reversal of type 1 diabetes in mice by brown adipose tissue transplant," Diabetes, Mar. 2012, 61: 674-682.

Harmon and Abumrad, "Binding of sulfosuccinimidyl fatty acids to adipocyte membrane proteins: Isolation and ammo-terminal sequence of an 88-kD protein implicated in transport of long-chain fatty acids," J Membr Biol., Apr. 1993, 133(1):43-9.
Haucke et al., "The effect of internal rotation on absorption and fluorescence of dye molecules," Journal of Molecular Structure, Mar. 1990, 219: 411-416.
Herrero et al., "Inflammation and adipose tissue macrophages in lipodystrophic mice," PNAS, Jan. 2010, 107: 240-245.
Himms-Hagen et al., "Multilocular fat cells in WAT of CL-316243-treated rats derive directly from white adipocytes," American Journal of Physiology Cell Physiology, 2000, 279: C670-681.
Hu et al., "Identification of brown adipose tissue in mice with fat-water IDEAL-MRI," Journal of Magnetic Resonance Imaging, 2010, 31: 1195-1202.
International Preliminary Report on Patentability in International Application No. PCT/US2014/054012, dated Mar. 8, 2016, 9 pages.
International Search Report and Written Opinion in International Application No. PCT/US2014/054012, dated Nov. 25, 2014, 15 pages.
Jamal and Saggerson, "Changes in brown-adipose-tissue mitochondrial processes in streptozotocin-diabetes," The Biochemical Journal, 1988, 252: 293-296.
Kajimura et al., "Regulation of the brown and white fat gene programs through a PRDM16/CtBP transcriptional complex," Genes & Development, 2008, 22: 1397-1409.
Kaplan et al., "Membrane proteins and urea and acetamide transport in the human erythrocyte," J. Membr Biol., Dec. 1975, 20:181-190.
Khanna and Branca, "Detecting brown adipose tissue activity with BOLD MRI in mice," Magnetic Resonance in Medicine, Oct. 2012, 68: 1285-1290.
Kim et al, "Effect of adipocyte beta3-adrenergic receptor activation on the type 2 diabetic MKR mice," American Journal of Physiology Endocrinology and Metabolism, Jun. 2006, 290: E1227-1236.
Madar et al., "18F-fluorobenzyl triphenyl phosphonium: a noninvasive sensor of brown adipose tissue thermogenesis," Journal of Nuclear Medicine, May 2011, 52(5): 808-814.
Massoud et al., "Molecular imaging in living subjects: seeing fundamental biological processes in a new light," Genes and Development, 2003, 17: 545-580.
Mattson, "Does brown fat protect against diseases of aging?," Ageing Research Reviews, Jan. 2010, 9: 69-76.
Nagajyothi et al., "Response of adipose tissue to early infection with *Trypanosoma cruzi* (Brazil strain)," The Journal of Infectious Diseases, 2012, 205: 830-840.
Nedergaard et al, "Unexpected evidence for active brown adipose tissue in adult humans," American Journal of Physiology Endocrinology and Metabolism, 2007, 293: E444-452.
Ocloo et al, "Cold-induced alterations of phospholipid fatty acyl composition in brown adipose tissue mitochondria are independent of uncoupling protein-1," American Journal of Physiology Regulatory, Integrative and Comparative Physiology, Sep. 2007, 293(3): R1086-1093.
Ouellet et al., "Brown adipose tissue oxidative metabolism contributes to energy expenditure during acute cold exposure in humans," The Journal of Clinical Investigation, 2012, 122: 545-552.
Pfannenberg et al., "Impact of age on the relationships of brown adipose tissue with sex and adiposity in humans," Diabetes, Jul. 2010, 59: 1789-1793.
Qiang et al., "Brown Remodeling of White Adipose Tissue by SirT1-Dependent Deacetylation of Pparγ," Cell, Aug. 2012, 150: 620-632.
Ran and Moore, "Spectral Unmixing Imaging of Wavelength-Responsive Fluorescent Probes: An Application for the Real-Time Report of Amyloid Beta Species in Alzheimer's Disease," Mol. Imaging Biol., Jun. 2012, 14(3): 293-300.
Ran et al., "Design, synthesis, and testing of difluoroboron derivatized curcumins as near infrared probes for in vivo detection of amyloid-β deposits," Journal of the American Chemical Society, Oct. 2009, 131(42): 15257-15261.
Richard and Picard, "Brown fat biology and thermogenesis," Frontiers in Bioscience, Jan. 2011, 16: 1233-1260.

(56) References Cited

OTHER PUBLICATIONS

Ryu et al., "Curcumin and Dehydrozingerone Derivatives: Synthesis, Radiolabeling, and Evaluation for β-Amyloid Plaque Imaging," J. Med. Chem, 2006, 49: 6111-6119.
Sandoval et al., "Fatty acid transport and activation and the expression patterns of genes involved in fatty acid trafficking," Arch. Biochem. Biophysics, Sep. 2008, 477:363-371.
Schulz et al., "Brown-fat paucity due to impaired BMP signalling induces compensatory browning of white fat," Nature, Mar. 2013, 495: 379-383.
Seydoux et al., "Brown adipose tissue metabolism in streptozotocin-diabetic rats," Endocrinology, 1983, 113: 604-610.
Shoup et al., "F-18 labeled bis-dialkylamino-curcuminoid as a potential amyloid-beta imaging agent," J Nucl Med, May 2011; 52:1538.
Tatsumi et al., "Intense (18)F-FDG uptake in brown fat can be reduced pharmacologically," Journal of Nuclear Medicine, Jul. 2004, 45(7): 1189-1193.
Tran and Kahn, "Transplantation of adipose tissue and stem cells: role in metabolism and disease," Nature Reviews Endocrinology, Apr. 2010, 6: 195-213.
Tseng et al., "New role of bone morphogenetic protein 7 in brown adipogenesis and energy expenditure," Nature, Aug. 2008, 454: 1000-1004.
Ulrich et al., "The Chemistry of Fluorescent Bodipy Dyes: Versatility Unsurpassed," Agnew Chem. Int. Ed., Feb. 2008, 47: 1184-1201.
van Marken Lichtenbelt et al., "Cold-activated brown adipose tissue in healthy men," The New England Journal of Medicine, Apr. 2009, 360: 1500-1508.
Weissleder, "A clearer vision for in vivo imaging," Nature Biotechnology, Apr. 2001, 19:316-317.
Williams and Fisher, "Globular warming: how fat gets to the furnace," Nat. Med., Feb. 2011, 17: 157-159.
Wilson-Fritch et al., "Mitochondrial remodeling in adipose tissue associated with obesity and treatment with rosiglitazone," The Journal of Clinical Investigation, Nov. 2004,114(9): 1281-1289.
Wu et al., "Brown adipose tissue can be activated or inhibited within an hour before 18F-FDG injection: a preliminary study with microPET," Journal of Biomedicine & Biotechnology, 2011, 2011: 159834.
Xu et al., "Exercise ameliorates high-fat diet-induced metabolic and vascular dysfunction, and increases adipocyte progenitor cell population in brown adipose tissue," American Journal of Physiology Regulatory, Integrative and Comparative Physiology, 2011, 300: R1115-1125.
Yang et al., "Curcumin Inhibits Formation of Amyloid Oligomers and Fibrils, Binds Plaques, and Reduces Amyloid in Vivo," J. Biol. Chem., 2005, 280: 5892-5901.
Yoneshiro et al., "Age-related decrease in cold-activated brown adipose tissue and accumulation of body fat in healthy humans," Obesity, Sep. 2011, 19: 1755-1760.
Zhang et al, "Cross talk between insulin and bone morphogenetic protein signaling systems in brown adipogenesis," Molecular and Cellular Biology, Sep. 2010, 30: 4224-4233.
Zhang et al., "Multi-Emissive Difluoroboron Dibenzoylmethane Polylactide Exhibiting Intense Fluorescence and Oxygen-Sensitive Room-Temperature Phosphorescence," J. Am. Chem. Soc., 2007, 129: 8942-8943.
Zhang, "In Vivo Optical Imaging of Interscapular Brown Adipose Tissue with 18F-FDG via Cerenkov Luminescence Imaging," Plos One, Apr. 2013, 8(4): e62007.
Zhou et al., "CD36 level and trafficking are determinants of lipolysis in adipocytes," Faseb J., Nov. 2012, 26(11):4733-42.
Office Action in U.S. Appl. No. 14/515,665, dated Jul. 26, 2016, 16 pages.
Office Action in U.S. Appl. No. 14/916,779, dated Oct. 24, 2016, 18 pages.
Office Action in U.S. Appl. No. 14/515,665, dated Feb. 24, 2017, 16 pages.

* cited by examiner

CURCUMIN ANALOGS

CROSS-REFERENCE TO RELATED APPLICATIONS

This application is a U.S. National Phase Application under 35 U.S.C. 0371 of International Patent Application No. PCT/US2013/053833, filed on Aug. 6, 2013, which claims priority to U.S. Provisional Application Ser. No. 61/742,264, filed on Aug. 6, 2012. Each application is incorporated by reference in its entirety herein.

FEDERALLY SPONSORED RESEARCH OR DEVELOPMENT

This invention was made with Government support under Grant No. K25AG036760 awarded by the National Institutes of Health. The Government has certain rights in the invention.

TECHNICAL FIELD

Provided herein are curcumin analogues that are able to interact with amyloid β (Aβ) and to attenuate the copper-induced crosslinking of Aβ. Also provided herein are methods of using the compounds in the treatment of Alzheimer's Disease or a related disorder.

BACKGROUND

High concentrations of metal ions such as copper and iron in the brain have been considered as an essential factor for the covalent crosslinking of Aβ, and thus an important trigger of the onset of amyloidosis pathology in Alzheimer's Disease (AD). Structurally, two imidazoliums of H13 and H14 of an Aβ peptide serve as essential binding sites for metal coordination. This coordination could bring two or more Aβ peptides into close proximity for initialization of irreversible Aβ crosslinking. Metal ion chelators have been tested for AD treatment with the purpose of retardation of Aβ aggregation. However, one of the obvious and potential side effects of the metal chelators is the disruption of brain metal homeostasis during prolonged treatment. Structurally, all of the reported chealtors are bi- or tri-dentate ligands for metal ions; therefore a single molecule could coordinate with a metal ion to form an intramolecular complex (FIG. 1a). Before reaching the target (or targeting region), they could sequester/seize metal ions that may be essential for normal brain functions.

SUMMARY

Provided herein are curcumin analogues that are able to specifically interact with amyloid β (Aβ) and to attenuate the copper-induced crosslinking of Aβ by competing for the copper binding sites within Aβ. Covalent crosslinking of Aβ is an important contributor to forming high molecular weight neurotoxic Aβ species. However, only a few compounds have been reported to data that can inhibit covalent crosslinking of Aβ. The coordination of copper with imidazolium on Histidine-13 and 14 (H13,1114) of Aβ peptides could be the source of initialization of covalent crosslinking. High copper concentrations in the brain have been considered as an important triggering factor for Alzheimer's disease (AD). We have previously demonstrated that curcumin analogues could be used as Near Infrared (NIR) and PET imaging probes for both soluble and insoluble Aβ species in vivo. See, for example, Ran, C. et al. *PLoS ONE* 6(4): e19362 (2011); Ran, C. et al. *JACS* 131:15257-15261 (2009); and Ran C. and Moore A. *Molecular Imaging and Biology* 14(3): 293-300 (2012), all of which are incorporated by reference in their entirety.

Provided herein is a compound of Formula (I)

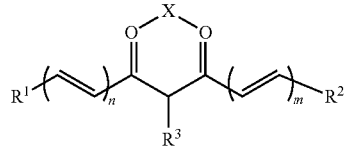

or a pharmaceutically acceptable salt thereof, wherein:

X is absent or selected from the group consisting of: $-CR^4R^5$ and $-BR^4R^5$;

$R^1$ is a substituted or unsubstituted aryl or a substituted or unsubstituted heteroaryl;

$R^2$ is a substituted or unsubstituted aryl or a substituted or unsubstituted heteroaryl;

$R^3$ is H or a $(C_1-C_6)$alkyl;

$R^4$ and $R^5$ are independently selected from the group consisting of H, halo, and $OR^6$;

$R^6$ is H or a $(C_1-C_6)$alkyl;

n and m are independently integers from 0-2, wherein at least one of n or m is not 0;

with the proviso that the wherein the compound is other than the following compounds, and salts thereof:

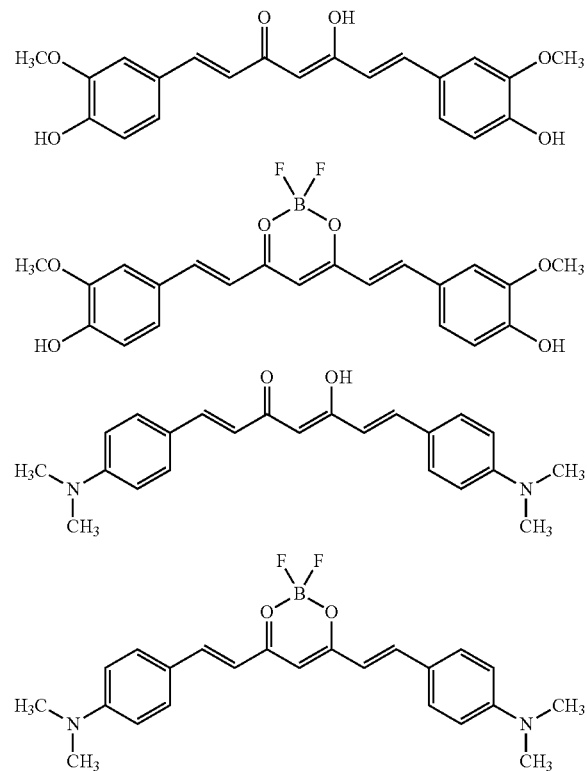

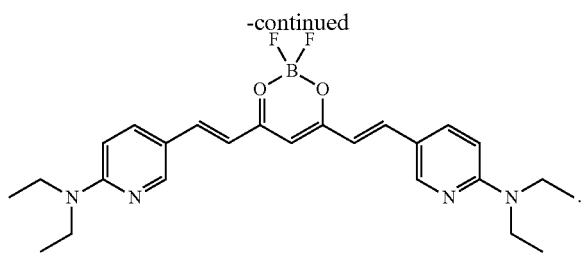

In some embodiments, a compound of Formula (I) can be a compound of Formula (II):

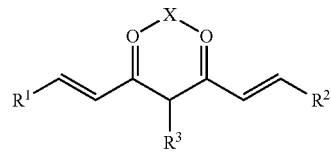

or a pharmaceutically acceptable salt thereof, wherein:

X is absent or selected from the group consisting of: —CR$^4$R$^5$ and —BR$^4$R$^5$;

R$^1$ is a substituted or unsubstituted aryl or a substituted or unsubstituted heteroaryl;

R$^2$ is a substituted or unsubstituted aryl or a substituted or unsubstituted heteroaryl;

R$^3$ is H or a (C$_1$-C$_6$)alkyl;

R$^4$ and R$^5$ are independently selected from the group consisting of H, halo, and OR$^6$;

R$^6$ is H or a (C$_1$-C$_6$)alkyl;

wherein the compound is other than the following compounds, and salts thereof:

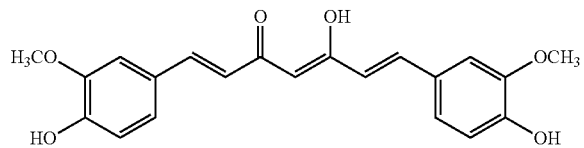

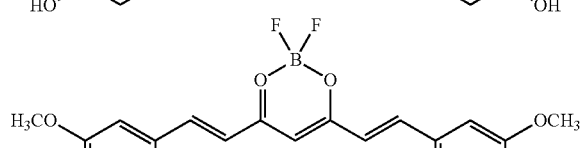

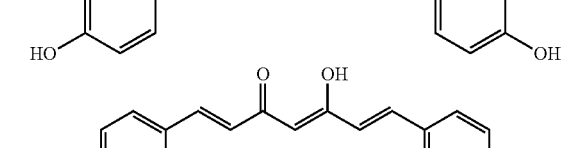

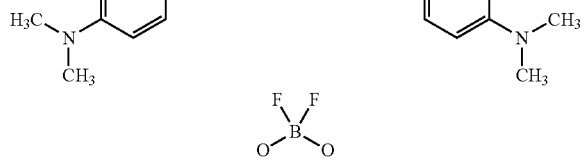

In some embodiments, a compound of Formula (I) can be a compound of Formula (III):

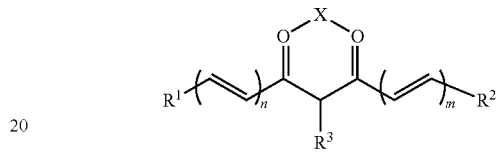

or a pharmaceutically acceptable salt thereof, wherein:

X is absent or selected from the group consisting of: —CR$^4$R$^5$ and —BR$^4$R$^5$;

R$^1$ is a substituted or unsubstituted aryl or a substituted or unsubstituted heteroaryl;

R$^2$ is a substituted or unsubstituted aryl or a substituted or unsubstituted heteroaryl;

R$^3$ is H or a (C$_1$-C$_6$)alkyl;

R$^4$ and R$^5$ are independently selected from the group consisting of H, halo, and OR$^6$;

R$^6$ is H or a (C$_1$-C$_6$)alkyl;

n and m are independently integers from 0-2, wherein at least one of n or m is not 0; and wherein R$^1$ and R$^2$ are different.

In any of the above embodiments, X can be —BR$^4$R$^5$. For example, R$^4$ and R$^5$ can be halo. In some embodiments, R$^4$ and R$^5$ are F.

In some embodiments, R$^1$ and R$^2$ are the same.

In some embodiments, R$^1$ and R$^2$ are independently:

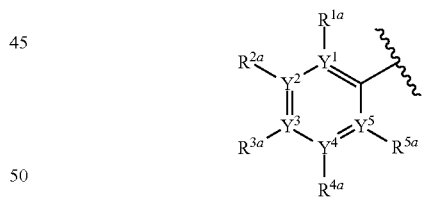

each Y$^1$, Y$^2$, Y$^3$, Y$^4$, and Y$^5$ is independently selected from C and N, wherein no more than two of Y$^1$, Y$^2$, Y$^3$, Y$^4$, and Y$^5$ is N;

R$^{1a}$, R$^{4a}$, and R$^{5a}$ are independently selected from the group consisting of: H, C$_{1-6}$ alkyl, C$_{2-6}$ alkenyl, C$_{2-6}$ alkynyl, halo, C$_{1-6}$ haloalkyl, CN, NO$_2$, OR$^a$, SR$^a$, C(O)R$^a$, C(O)NR$^a$R$^b$, C(O)OR$^a$, OC(O)R$^a$, NR$^a$R$^b$, NR$^a$C(O)R$^b$, NR$^a$C(O)OR$^b$, S(O)R$^a$, S(O)$_2$R$^a$, a substituted or unsubstituted aryl, and a substituted or unsubstituted heteroaryl;

R$^{2a}$ is selected from the group consisting of: H, C$_{1-6}$ alkyl, C$_{2-6}$ alkenyl, C$_{2-6}$ alkynyl, halo, C$_{1-6}$ haloalkyl, CN, NO$_2$, SR$^a$, C(O)R$^a$, C(O)NR$^a$R$^b$, C(O)OR$^a$, OC(O)R$^a$, NR$^a$R$^b$, NR$^a$C(O)R$^b$, NIVC(O)OR$^b$, S(O)R$^a$, S(O)$_2$R$^a$, a substituted or unsubstituted aryl, and a substituted or unsubstituted heteroaryl;

$R^{3a}$ is selected from the group consisting of: H, $C_{1-6}$ alkyl, $C_{2-6}$ alkenyl, $C_{2-6}$ alkynyl, halo, $C_{1-6}$ haloalkyl, CN, $NO_2$, $SR^a$, $C(O)R^a$, $C(O)NR^aR^b$, $C(O)OR^a$, $OC(O)R^a$, $NR^aC(O)R^b$, $NR^aC(O)OR^b$, $S(O)R^a$, $S(O)_2R^a$, a substituted or unsubstituted aryl, and a substituted or unsubstituted heteroaryl; and each $R^a$ and $R^b$ is independently selected from H, $C_{1-6}$ alkyl, aryl, and heteroaryl.

In some embodiments, at least one of $R^1$ and $R^2$ is a substituted or unsubstituted heteroaryl. For example, the heteroaryl can be a N-containing heteroaryl. In some embodiments, the N-containing heteroaryl is an imidazolyl. For example, the N-containing heteroaryl is selected from the group consisting of:

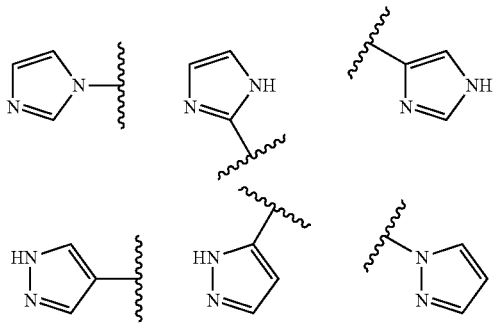

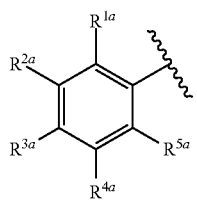

wherein each heteroaryl is substituted or unsubstituted.

In some embodiments, $R^1$ and $R^2$ are each independently a substituted aryl. For example, $R^1$ and $R^2$ can be independently:

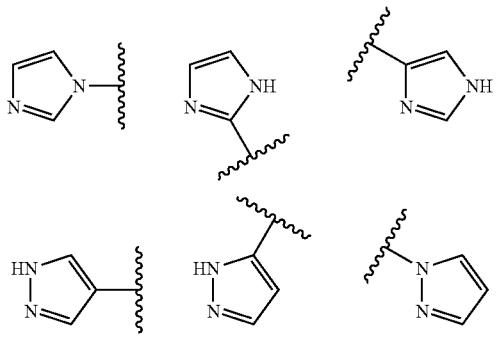

wherein:
$R^{1a}$, $R^{4a}$, and $R^{5a}$ are independently selected from the group consisting of: H, $C_{1-6}$ alkyl, $C_{2-6}$ alkenyl, $C_{2-6}$ alkynyl, halo, $C_{1-6}$ haloalkyl, CN, $NO_2$, $OR^a$, $SR^a$, $C(O)R^a$, $C(O)NR^aR^b$, $C(O)OR^a$, $OC(O)R^a$, $NR^aR^b$, $NR^aC(O)R^b$, $NR^aC(O)OR^b$, $S(O)R^a$, $S(O)_2R^a$, a substituted or unsubstituted aryl, and a substituted or unsubstituted heteroaryl;

$R^{2a}$ is selected from the group consisting of: H, $C_{1-6}$ alkyl, $C_{2-6}$ alkenyl, $C_{2-6}$ alkynyl, halo, $C_{1-6}$ haloalkyl, CN, $NO_2$, $SR^a$, $C(O)R^a$, $C(O)NR^aR^b$, $C(O)OR^a$, $OC(O)R^a$, $NR^aR^b$, $NR^aC(O)R^b$, $NR^aC(O)OR^b$, $S(O)R^a$, $S(O)_2R^a$, a substituted or unsubstituted aryl, and a substituted or unsubstituted heteroaryl;

$R^{3a}$ is selected from the group consisting of: H, $C_{1-6}$ alkyl, $C_{2-6}$ alkenyl, $C_{2-6}$ alkynyl, halo, $C_{1-6}$ haloalkyl, CN, $NO_2$, $SR^a$, $C(O)R^a$, $C(O)NR^aR^b$, $C(O)OR^a$, $OC(O)R^a$, $NR^aC(O)R^b$, $NR^aC(O)OR^b$, $S(O)R^a$, $S(O)_2R^a$, a substituted or unsubstituted aryl, and a substituted or unsubstituted heteroaryl; and each $R^a$ and $R^b$ is independently selected from H, $C_{1-6}$ alkyl, aryl, and heteroaryl.

In some embodiments, $R^a$ and $R^b$ is independently selected from H and $C_{1-6}$ alkyl.

In some embodiments, $R^{3a}$ is a substituted or unsubstituted heteroaryl. For example, the heteroaryl is a N-containing heteroaryl. In some embodiments, the N-containing heteroaryl is an imidazolyl. For example, the N-containing heteroaryl is selected from the group consisting of:

wherein each heteroaryl is substituted or unsubstituted.

Non-limiting examples of a compound of Formula (I) (e.g., a compound of Formula(II) and/or Formula (III)) is selected from the group consisting of:

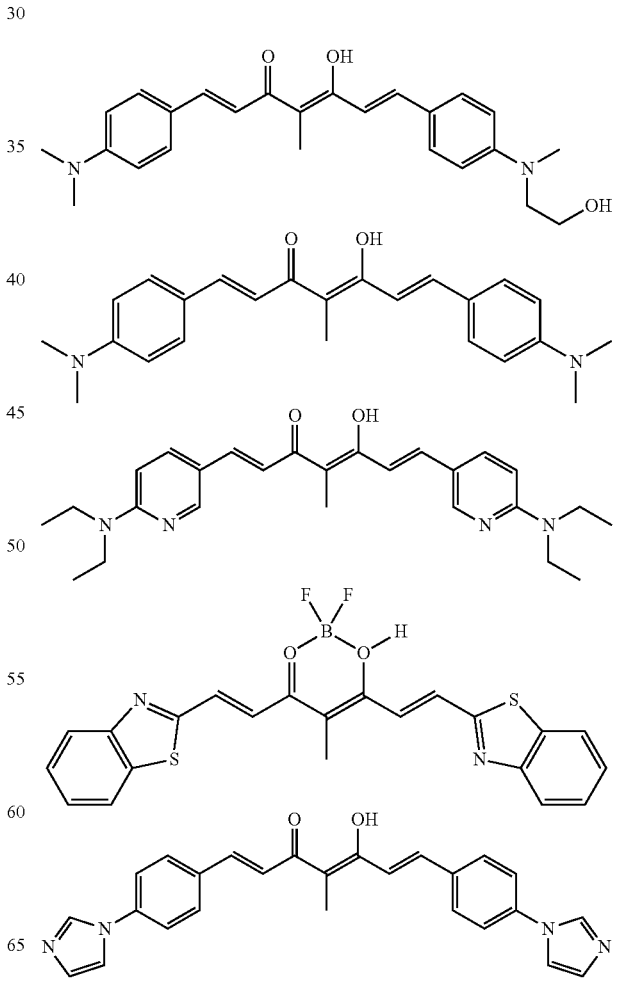

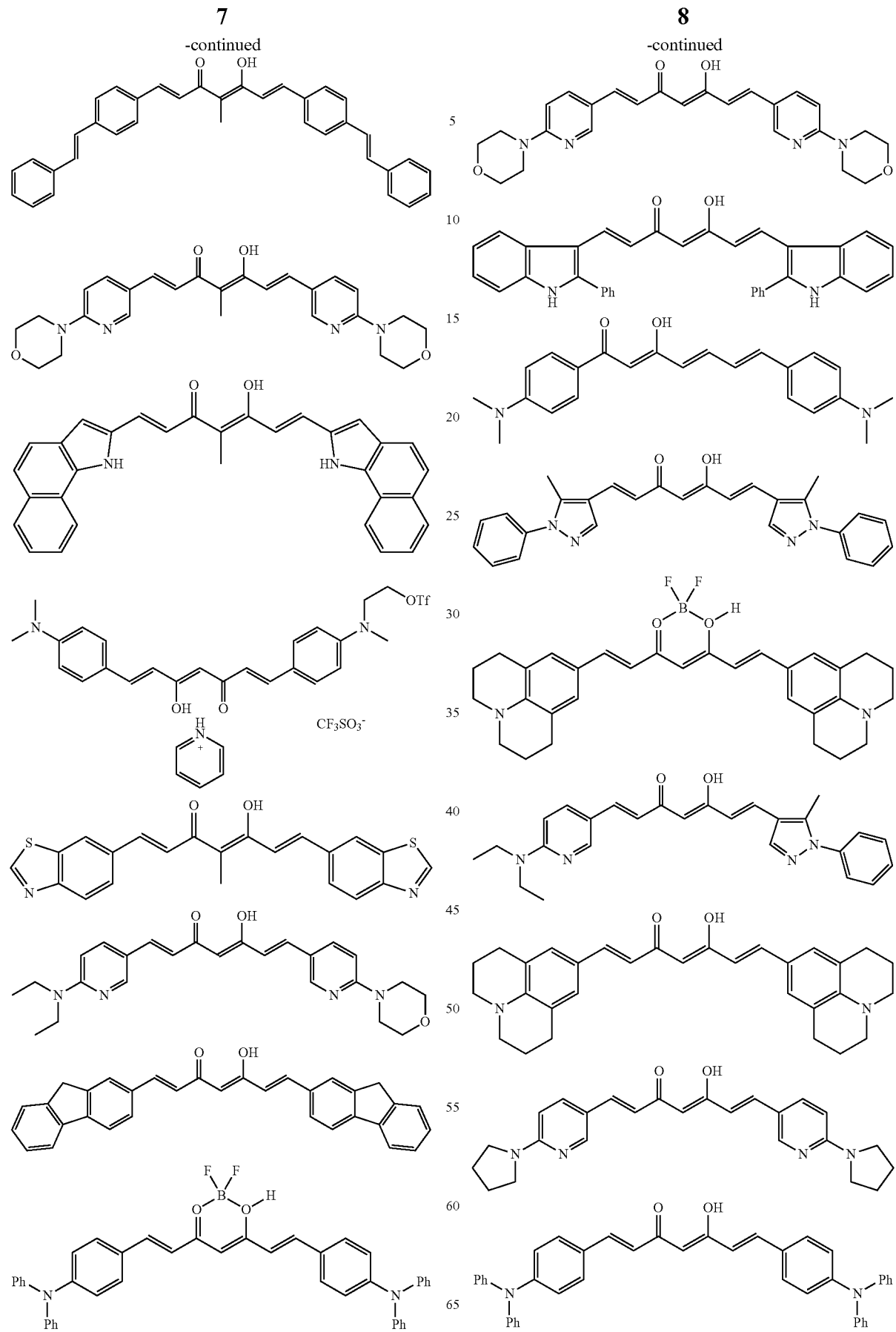

-continued
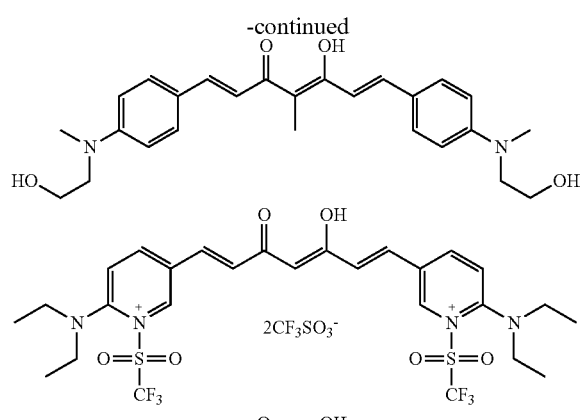
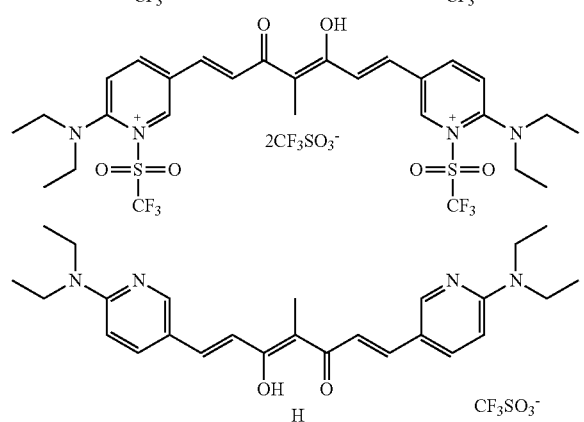
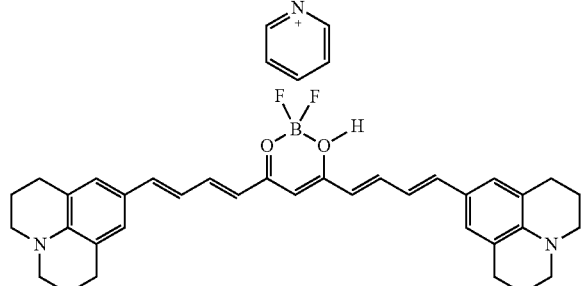
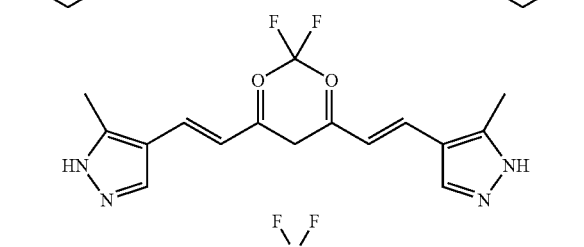
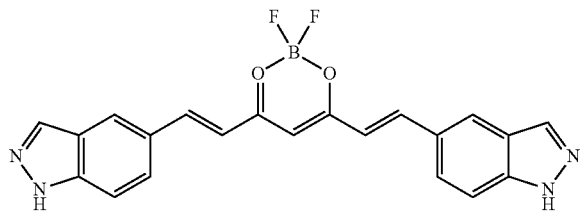
-continued
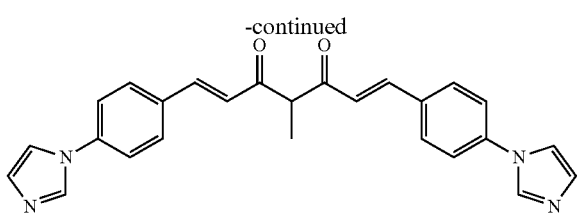
or a pharmaceutically acceptable salt form thereof.
In some embodiments, the compound of Formula (I) is selected from the group consisting of:
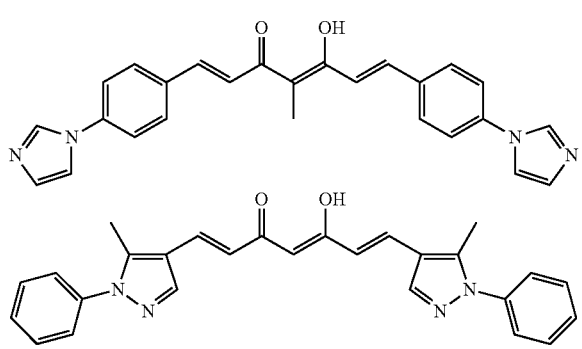
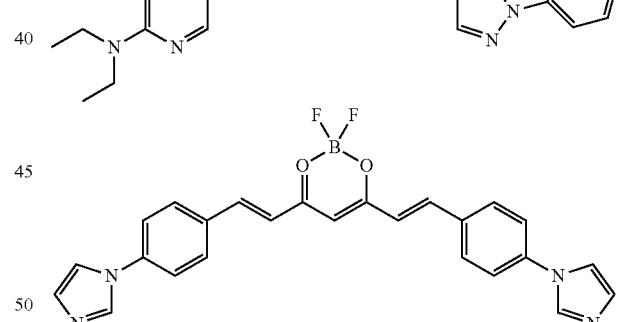
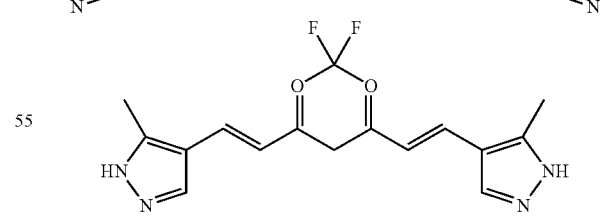
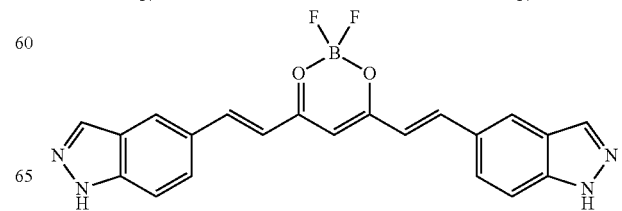

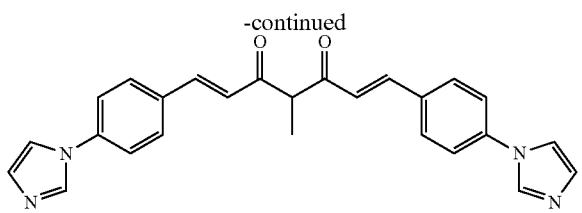

or a pharmaceutically acceptable salt thereof.

Also provided herein is a pharmaceutical composition comprising a compound as provided herein, or a pharmaceutically acceptable salt thereof, and a pharmaceutically acceptable excipient.

The compound provided herein may be useful for treating Alzheimer's Disease or a related disorder in a patient. Accordingly, provided herein is a method including administering to the patient a therapeutically effective amount of a compound provided herein, or a pharmaceutically acceptable salt thereof.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 6 shows SDS-PAGE gel electrophoresis and Western blotting of Aβ42 species with curcumin, CRANAD-3, and CRANAD-17.

FIG. 8 shows the therapeutic effectiveness of CRANAD-17.

DETAILED DESCRIPTION

Definitions

Figure 1B:
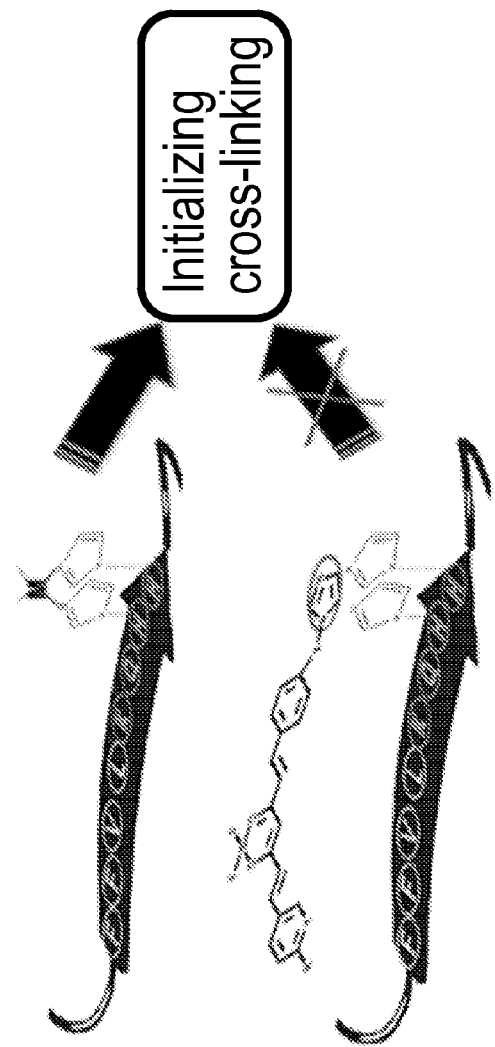
FIG. 1b shows the bidentate compound coordinating with copper to form an intramolecular complex (top) and the proposed interaction model between Aβ (the HHQKLVFF segment shown; bottom).
Figure 1A:
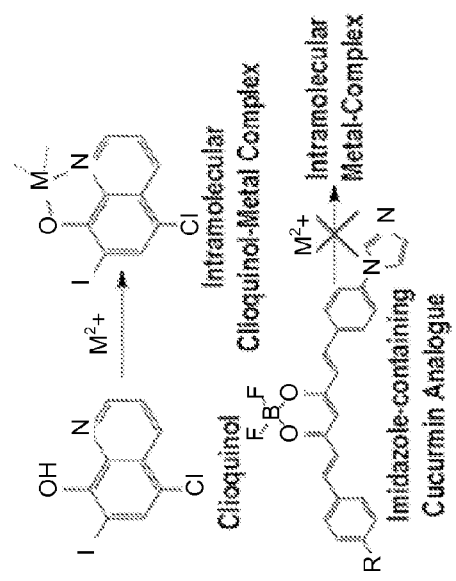
FIG. 1a shows clioquinol, a known bidentate ligand for copper and a designed mono-dentate imidazolium-containing curcumin analogue.

For the terms "for example" and "such as," and grammatical equivalences thereof, the phrase "and without limitation" is understood to follow unless explicitly stated otherwise. As used herein, the term "about" is meant to account for variations due to experimental error. All measurements reported herein are understood to be modified by the term "about", whether or not the term is explicitly used, unless explicitly stated otherwise. As used herein, the singular forms "a," "an," and "the" include plural referents unless the context clearly dictates otherwise.

A "patient," as used herein, includes both humans and other animals, particularly mammals. Thus, the methods are applicable to both human therapy and veterinary applications. In some embodiments, the patient is a mammal, for example, a primate. In some embodiments, the patient is a human.

A "therapeutically effective" amount of a compound provided herein is typically one which is sufficient to achieve the desired effect and may vary according to the nature and severity of the disease condition, and the potency of the compound. It will be appreciated that different concentrations may be employed for prophylaxis than for treatment of an active disease.

The term, "compound," as used herein is meant to include all stereoisomers, geometric isomers, and tautomers of the structures depicted. Compounds herein identified by name or structure as one particular tautomeric form are intended to include other tautomeric forms unless otherwise specified.

In some embodiments, a compound provided herein, or salt thereof, is substantially isolated. By "substantially isolated" is meant that the compound is at least partially or substantially separated from the environment in which it was formed or detected. Partial separation can include, for example, a composition enriched in the compound provided herein. Substantial separation can include compositions containing at least about 50%, at least about 60%, at least about 70%, at least about 80%, at least about 90%, at least about 95%, at least about 97%, or at least about 99% by weight of the compound provided herein, or salt thereof. Methods for isolating compounds and their salts are routine in the art.

The term "alkyl" includes straight-chain alkyl groups (e.g., methyl, ethyl, propyl, butyl, pentyl, hexyl, heptyl, octyl, nonyl, and decyl) and branched-chain alkyl groups (isopropyl, tert-butyl, isobutyl, and sec-butyl), cycloalkyl (alicyclic) groups (cyclopropyl, cyclopentyl, cyclohexyl, cycloheptyl, and cyclooctyl), alkyl substituted cycloalkyl groups, and cycloalkyl substituted alkyl groups. In certain embodiments, a straight chain or branched chain alkyl has six or fewer carbon atoms in its backbone (e.g., $C_1$-$C_6$ for straight chain; $C_3$-$C_6$ for branched chain). The term $C_1$-$C_6$ includes alkyl groups containing 1 to 6 carbon atoms.

The term "alkenyl" includes aliphatic groups that may or may not be substituted, as described above for alkyls, containing at least one double bond and at least two carbon atoms. For example, the term "alkenyl" includes straight-chain alkenyl groups (e.g., ethenyl, propenyl, butenyl, pentenyl, hexenyl, heptenyl, octenyl, nonenyl, and decenyl) and branched-chain alkenyl groups. In certain embodiments, a straight chain or branched chain alkenyl group has twelve or fewer carbon atoms in its backbone (e.g., $C_2$-$C_{12}$ for straight chain; $C_3$-$C_{12}$ for branched chain). The term $C_2$-$C_{12}$ includes alkenyl groups containing 2 to 12 carbon atoms.

The term "alkynyl" includes unsaturated aliphatic groups analogous in length and possible substitution to the alkyls described above, but which contain at least one triple bond and two carbon atoms. For example, the term "alkynyl" includes straight-chain alkynyl groups (e.g., ethynyl, propynyl, butynyl, pentynyl, hexynyl, heptynyl, octynyl, nonynyl, and decynyl) and branched-chain alkynyl groups. In certain embodiments, a straight chain or branched chain alkynyl group has twelve or fewer carbon atoms in its backbone (e.g., $C_2$-$C_{12}$ for straight chain; $C_3$-$C_{12}$ for branched chain). The term $C_2$-$C_{12}$ includes alkynyl groups containing 2 to 12 carbon atoms.

The term "alkoxy" is used in its conventional sense, and refers to alkyl groups linked to molecules via an oxygen atom. In some embodiments, an alkoxy has twelve or fewer carbon atoms in its backbone (e.g., a $C_1$-$C_{12}$ alkoxy). For example, $C_1$-$C_{10}$, $C_1$-$C_8$, $C_1$-$C_6$, $C_1$-$C_4$, $C_1$-$C_3$, or $C_1$-$C_2$. Non-limiting examples of an alkoxy group include methoxy, ethoxy, propoxy, butoxy, and hexoxy.

The terms "halo" or "halogen", used alone or in combination with other terms, refers to fluoro, chloro, bromo and iodo.

The term "haloalkyl" refers to an alkyl group in which one or more of the hydrogen atoms has been replaced by a halogen atom. The term "$C_n$-$C_m$ haloalkyl" refers to a $C_n$-$C_m$ alkyl group having n to m carbon atoms, and from at least one up to $\{2(n \text{ to } m)+1\}$ halogen atoms, which may either be the same or different. In some embodiments, the halogen atoms are fluoro atoms. In some embodiments, the haloalkyl group has 1 to 6 or 1 to 4 carbon atoms. Example haloalkyl groups include $CF_3$, $C_2F_5$, $CHF_2$, $CCl_3$, $CHCl_2$, $C_2Cl_5$ and the like. In some embodiments, the haloalkyl group is a fluoroalkyl group.

The term "haloalkoxy", employed alone or in combination with other terms, refers to a group of formula —O-haloalkyl, wherein the haloalkyl group is as defined above. The term "$C_n$-$C_m$ haloalkoxy" refers to a haloalkoxy group, the haloalkyl group of which has n to m carbons. Example haloalkoxy groups include trifluoromethoxy and the like. In some embodiments, the haloalkoxy group has 1 to 6, 1 to 4, or 1 to 3 carbon atoms.

The term "aromatic" refers to a carbocycle or heterocycle having one or more polyunsaturated rings having aromatic character (i.e., having (4n+2) delocalized π (pi) electrons where n is an integer).

The term "carbocyclyl" includes a cyclic aliphatic group which may be saturated or unsaturated. For example, carbocyclyl groups include cyclopropyl, cyclopentyl, cyclohexyl, cycloheptyl, and cyclooctyl. In some embodiments, carbocyclyls have from 3-8 carbon atoms in their ring structure, for example, they can have 3, 4, 5 or 6 carbons in the ring structure.

In general, the term "aryl" includes groups, including 5- and 6-membered single-ring aromatic groups, such as benzene and phenyl. Furthermore, the term "aryl" includes multicyclic aryl groups, e.g., tricyclic, bicyclic, such as naphthalene and anthracene.

The term "heteroaryl" includes groups, including 5- and 6-membered single-ring aromatic groups, that have from one to four heteroatoms, for example, pyrrole, furan, thiophene, thiazole, isothiaozole, imidazole, triazole, tetrazole, pyrazole, oxazole, isooxazole, pyridine, pyrazine, pyridazine, and pyrimidine, and the like. Furthermore, the term "heteroaryl" includes multicyclic heteroaryl groups, e.g., tricyclic, bicyclic, such as benzoxazole, benzodioxazole, benzothiazole, benzoimidazole, benzothiophene, methylenedioxyphenyl, quinoline, isoquinoline, napthyridine, indole, benzofuran, purine, benzofuran, quinazoline, deazapurine, indazole, or indolizine.

The term "heterocyclyl" includes non-aromatic groups, including but not limited to, 3- to 10-membered single or multiple non-aromatic rings having one to five heteroatoms, for example, oxetane, piperazine, pyrrolidine, piperidine, or homopiperazine.

The term "substituted" means that an atom or group of atoms replaces hydrogen as a "substituent" attached to another group. For aryl and heteroaryl groups, the term "substituted", unless otherwise indicated, refers to any level of substitution, namely mono, di, tri, tetra, or penta substitution, where such substitution is permitted. The substituents are independently selected, and substitution may be at any chemically accessible position. In some cases, two sites of substitution may come together to form a 3-10 membered carbocyclyl or heterocyclyl ring.

Substituents include, but are not limited to, $Cy^1$, $C_{1-6}$ alkyl, $C_{2-6}$ alkenyl, $C_{2-6}$) alkynyl, halo, $C_{1-6}$ haloalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$ and $S(O)_2NR^{c1}R^{d1}$;

each $Cy^1$ is independently $C_{6-10}$ aryl, $C_{3-10}$ carbocyclyl, 5-10 membered heteroaryl or 4-10 membered heterocyclyl, each of which is unsubstituted or substituted by 1, 2, 3, 4 or 5 substituents independently selected from $C_{1-6}$ alkyl, $C_{2-6}$ alkenyl, $C_{2-6}$ alkynyl, halo, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $SO)NR^{c1}R^{d1}$, $S(O)R^{b1}$, $S(O)_2NR^{c1}R^{d1}$ and oxo;

each $R^{a1}$, $R^{b1}$, $R^{c1}$, $R^{d1}$, is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ carbocyclyl, 5-10 membered heteroaryl, 4-10 membered heterocyclyl, $C_{6-10}$ aryl-$C_{1-4}$ alkyl, $C_{3-10}$ carbocyclyl-$C_{1-4}$ alkyl, (5-10 membered heteroaryl)-$C_{1-4}$ alkyl or (4-10 membered heterocyclyl)-$C_{1-4}$ alkyl, wherein said $C_{1-6}$ alkyl, $C_{2-6}$ alkenyl, $C_{2-6}$ alkynyl, $C_{6-10}$ aryl, $C_{3-10}$ carbocyclyl, 5-10 membered heteroaryl, 4-10 membered heterocyclyl, $C_{6-10}$ aryl-$C_{1-4}$ alkyl, $C_{3-10}$ carbocyclyl-$C_{1-4}$ alkyl, (5-10 membered heteroaryl)-$C_{1-4}$ alkyl and (4-10 membered heterocyclyl)-$C_{1-4}$ alkyl is optionally substituted with 1, 2, 3, 4, or 5 substituents independently selected from $C_{1-4}$ alkyl, $C_{1-4}$ haloalkyl, halo, CN, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b}4$, $NR^{c4}C(O)NR^{c4}R^{d4}$, $NR^{c4}C(O)OR^{a4}$, $C(=NR^{e4})NR^{c4}R^{d4}$, $S(O)R^{b4}$, $S(O)NR^{c4}R^{d4}$, $S(O)_2R^{b4}$, $NR^{c4}S(O)_2R^{b4}$, $NR^{c4}S(O)_2NR^{c4}R^{d4}$ and $S(O)_2NR^{c4}R^{d4}$;

each $R^{a4}$, $R^{b4}$, $R^{c4}$ and $R^{d4}$ is independently selected from H, $C_{1-4}$ alkyl, $C_{1-4}$ haloalkyl, $C_{2-4}$ alkenyl and $C_{2-4}$ alkynyl, wherein said $C_{1-4}$ alkyl, $C_{2-4}$ alkenyl, and $C_{2-4}$ alkynyl, is optionally substituted with 1, 2, or 3 substituents independently selected from OH, CN, amino, halo, $C_{1-4}$ alkyl, $C_{1-4}$ alkoxy, $C_{1-4}$ alkylthio, $C_{1-4}$ alkylamino, di($C_{1-4}$ alkyl)amino, $C_{1-4}$ haloalkyl, and $C_{1-4}$ haloalkoxy.

Where substituent groups are specified by their conventional chemical formulas, written from left to right, they equally encompass the chemically identical substituents that would result from writing the structure from right to left, for example, —CH$_2$O— is equivalent to —OCH$_2$—. In some embodiments, one or more substituents can be a group reactive with a biologically active molecule or a detectable agent.

As used herein, chemical structures which contain one or more stereocenters depicted with dashed and bold bonds (i.e., ) are meant to indicate absolute stereochemistry of the stereocenter(s) present in the chemical structure. As used herein, bonds symbolized by a simple line do not indicate a stereo-preference. Unless otherwise indicated, chemical structures, which include one or more stereocenters, illustrated herein without indicating absolute or relative stereochemistry encompass all possible stereoisomeric forms of the compound (e.g., diastereomers, enantiomers) and mixtures thereof (e.g., racemic mixtures). Structures with a single bold or dashed line, and at least one additional simple line, encompass a single enantiomeric series of all possible diastereomers.

Resolution of racemic mixtures of compounds can be carried out by any of numerous methods known in the art. An exemplary method includes fractional recrystallization using a chiral resolving acid which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid, or the various optically active camphorsulfonic acids such as camphorsulfonic acid. Other resolving agents suitable for fractional crystallization methods include stereoisomerically pure forms of methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent compositions can be determined by one skilled in the art.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "salt" includes any ionic form of a compound and one or more counter-ionic species (cations and/or anions). Salts also include zwitterionic compounds (i.e., a molecule containing one more cationic and anionic species, e.g., zwitterionic amino acids). Counter ions present in a salt can include any cationic, anionic, or zwitterionic species. Exemplary anions include, but are not limited to: chloride, bromide, iodide, nitrate, sulfate, bisulfate, sulfite, bisulfite, phosphate, acid phosphate, perchlorate, chlorate, chlorite, hypochlorite, periodate, iodate, iodite, hypoiodite, carbonate, bicarbonate, isonicotinate, acetate, trichloroacetate, trifluoroacetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, trifluoromethanesulfonate, ethanesulfonate, benzenesulfonate, p-toluenesulfonate, p-trifluoromethylbenzenesulfonate, hydroxide, aluminates, and borates. Exemplary cations include, but are not limited to: monovalent alkali metal cations, such as lithium, sodium, potassium, and cesium, and divalent alkaline earth metals, such as beryllium, magnesium, calcium, strontium, and barium. Also included are transition metal cations, such as gold, silver, copper and zinc, as well as non-metal cations, such as ammonium salts.

Also provided herein are pharmaceutically acceptable salts of the compounds described herein. As used herein, "pharmaceutically acceptable salts" refers to derivatives of the disclosed compounds wherein the parent compound is modified by converting an existing acid or base moiety to its salt. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the compounds provided herein include the conventional non-toxic salts of the parent compound formed, for example, from non-toxic inorganic or organic acids. The pharmaceutically acceptable salts of the compounds provided herein can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; in some embodiments, a non-aqueous media like ether, ethyl acetate, alcohols (e.g., methanol, ethanol, isopropanol, or butanol) or acetonitrile (ACN) can be used. Lists of suitable salts are found in *Remington's Pharmaceutical Sciences*, 17th ed., Mack Publishing Company, Easton, Pa., 1985, p. 1418 and *Journal of Pharmaceutical Science*, 66, 2 (1977). Conventional methods for preparing salts are described, for example, in *Handbook of Pharmaceutical Salts: Properties, Selection, and Use*, Wiley-VCH, 2002.

The term "essentially pure" refers to chemical purity of a compound provided herein that may be substantially or essentially free of other components which normally accompany or interact with the compound prior to purification. By way of example only, a compound may be "essentially pure" when the preparation of the compound contains less than about 30%, less than about 25%, less than about 20%, less than about 15%, less than about 10%, less than about 5%, less than about 4%, less than about 3%, less than about 2%, or less than about 1% (by dry weight) of contaminating components. Thus, an "essentially pure" compound may have a purity level of about 70%, about 75%, about 80%, about 85%, about 90%, about 95%, about 96%, about 97%, about 98%, about 99% or greater. For the purposes of this document, preparations of functionalized polymers or conjugates differing only in the length of their polymer chain are considered to be essentially pure. An essentially pure compound may be obtained using chromatographic purification methods.

Compounds

Provided herein are curcumin analogues that are able to specifically interact with amyloid β (Aβ) and to attenuate the copper-induced crosslinking of Aβ by competing for the copper binding sites within Aβ.

In some embodiments, a curcumin analog as provided herein is a compound of Formula (I):

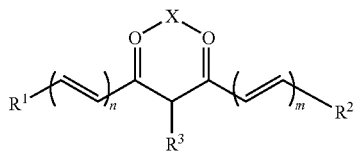

or a pharmaceutically acceptable salt thereof,
wherein:
X is absent or selected from the group consisting of: —CR$^4$R$^5$ and —BR$^4$R$^5$;
R$^1$ is a substituted or unsubstituted aryl or a substituted or unsubstituted heteroaryl;
R$^2$ is a substituted or unsubstituted aryl or a substituted or unsubstituted heteroaryl;
R$^3$ is H or a (C$_1$-C$_6$)alkyl;
R$^4$ and R$^5$ are independently selected from the group consisting of H, halo, and OR$^6$;
R$^6$ is H or a (C$_1$-C$_6$)alkyl;
n and m are independently integers from 0-2, wherein at least one of n or m is not 0.

In some embodiments, a compound of Formula (I) is other than the following compounds, and salts thereof:

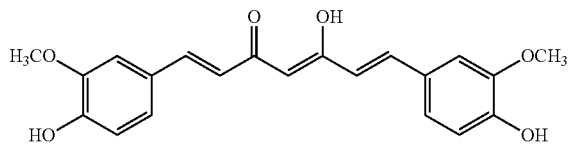

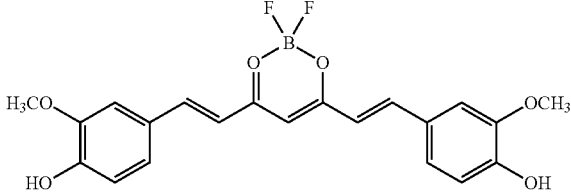

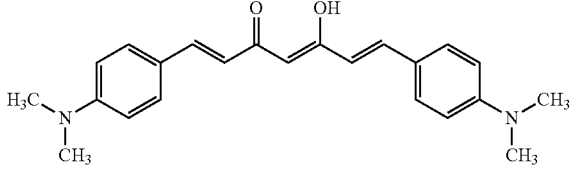

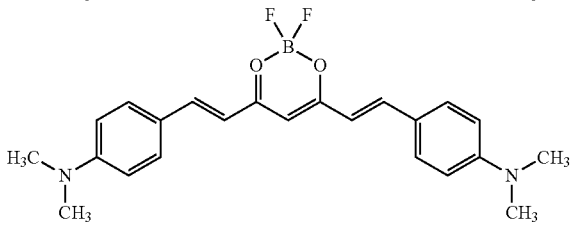

In some embodiments, X is —BR$^4$R$^5$. For example, R$^4$ and R$^5$ are halo. In some embodiments, R$^4$ and R$^5$ are F. In some embodiments, X is —CR$^4$R$^5$. For example, in some such embodiments, R$^4$ and R$^5$ are halo. In some embodiments, X is absent. In some embodiments, R$^4$ and R$^5$ are F. In some embodiments, n and m are each 1. In some embodiments, n is 0 and m is 1 or 2. In some embodiments, n is 1 and m is 2.

In some embodiments, R$^1$ and R$^2$ are independently:

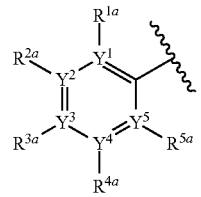

each Y$^1$, Y$^2$, Y$^3$, Y$^4$, and Y$^5$ is independently selected from C and N, wherein no more than two of Y$^1$, Y$^2$, Y$^3$, Y$^4$, and Y$^5$ is N;

R$^{1a}$, R$^{4a}$, and R$^{5a}$ are independently selected from the group consisting of: H, C$_{1-6}$ alkyl, C$_{2-6}$ alkenyl, C$_{2-6}$ alkynyl, halo, C$_{1-6}$ haloalkyl, CN, NO$_2$, OR$^a$, SR$^a$, C(O)R$^a$, C(O)NR$^a$R$^b$, C(O)OR$^a$, OC(O)R$^a$, NR$^a$R$^b$, NR$^a$C(O)R$^b$, NR$^a$C(O)OR$^b$, S(O)R$^a$, S(O)$_2$R$^a$, a substituted or unsubstituted aryl, and a substituted or unsubstituted heteroaryl;

R$^{2a}$ is selected from the group consisting of: H, C$_{1-6}$ alkyl, C$_{2-6}$ alkenyl, C$_{2-6}$ alkynyl, halo, C$_{1-6}$ haloalkyl, CN, NO$_2$, SR$^a$, C(O)R$^a$, C(O)NR$^a$R$^b$, C(O)OR$^a$, OC(O)R$^a$, NR$^a$R$^b$, NR$^a$C(O)R$^b$, NR$^a$C(O)OR$^b$, S(O)R$^a$, S(O)$_2$R$^a$, a substituted or unsubstituted aryl, and a substituted or unsubstituted heteroaryl;

R$^{3a}$ is selected from the group consisting of: H, C$_{1-6}$ alkyl, C$_{2-6}$ alkenyl, C$_{2-6}$ alkynyl, halo, C$_{1-6}$ haloalkyl, CN, NO$_2$, SR$^a$, C(O)R$^a$, C(O)NR$^a$R$^b$, C(O)OR$^a$, OC(O)R$^a$, NR$^a$C(O)R$^b$, NR$^a$C(O)OR$^b$, S(O)R$^a$, S(O)$_2$R$^a$, a substituted or unsubstituted aryl, and a substituted or unsubstituted heteroaryl;

each R$^a$ and R$^b$ is independently selected from H, C$_{1-6}$ alkyl, aryl, and heteroaryl; and wherein when any of Y$^1$, Y$^2$, Y$^3$, Y$^4$, or Y$^5$ is N, the corresponding R$^{1a}$, R$^{2a}$, R$^{3a}$, R$^{4a}$, and R$^{5a}$ is absent.

In some embodiments, Y$^4$ is N. In some embodiments, R$^a$ and R$^b$ are independently selected from H and C$_{1-6}$ alkyl.

In some embodiments, R$^1$ and R$^2$ are each independently a substituted aryl. For example, R$^1$ and R$^2$ can be independently:

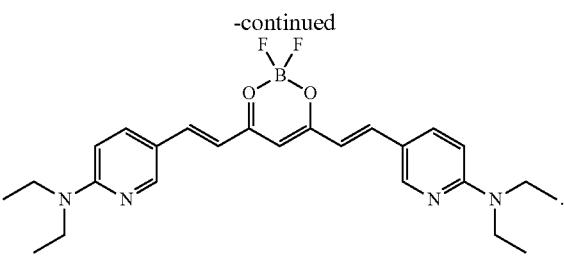

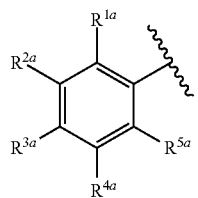

wherein:

$R^{1a}$, $R^{4a}$, and $R^{5a}$ are independently selected from the group consisting of: H, $C_{1-6}$ alkyl, $C_{2-6}$ alkenyl, $C_{2-6}$ alkynyl, halo, $C_{1-6}$ haloalkyl, CN, $NO_2$, $OR^a$, $SR^a$, $C(O)R^a$, $C(O)NR^aR^b$, $C(O)OR^a$, $OC(O)R^a$, $NR^aR^b$, $NR^aC(O)R^b$, $NR^aC(O)OR^b$, $S(O)R^a$, $S(O)_2R^a$, a substituted or unsubstituted aryl, and a substituted or unsubstituted heteroaryl;

$R^{2a}$ is selected from the group consisting of: H, $C_{1-6}$ alkyl, $C_{2-6}$ alkenyl, $C_{2-6}$ alkynyl, halo, $C_{1-6}$ haloalkyl, CN, $NO_2$, $SR^a$, $C(O)R^a$, $C(O)NR^aR^b$, $C(O)OR^a$, $OC(O)R^a$, $NR^aR^b$, $NR^aC(O)R^b$, $NR^aC(O)OR^b$, $S(O)R^a$, $S(O)_2R^a$, a substituted or unsubstituted aryl, and a substituted or unsubstituted heteroaryl;

$R^{3a}$ is selected from the group consisting of: H, $C_{1-6}$ alkyl, $C_{2-6}$ alkenyl, $C_{2-6}$ alkynyl, halo, $C_{1-6}$ haloalkyl, CN, $NO_2$, $SR^a$, $C(O)R^a$, $C(O)NR^aR^b$, $C(O)OR^a$, $OC(O)R^a$, $NR^aC(O)R^b$, $NR^aC(O)OR^b$, $S(O)R^a$, $S(O)_2R^a$, a substituted or unsubstituted aryl, and a substituted or unsubstituted heteroaryl; and each $R^a$ and $R^b$ is independently selected from H, $C_{1-6}$ alkyl, aryl, and heteroaryl.

In some embodiments, $R^{3a}$ and $R^b$ is independently selected from H and $C_{1-6}$ alkyl.

In some embodiments, $R^{3a}$ is a substituted or unsubstituted heteroaryl. In some embodiments, $R^{3a}$ is a substituted or unsubstituted N-containing heteroaryl. For example, the N-containing heteroaryl can be an imidazolyl. Non-limiting examples of imidazolyls and pyrazolyls include:

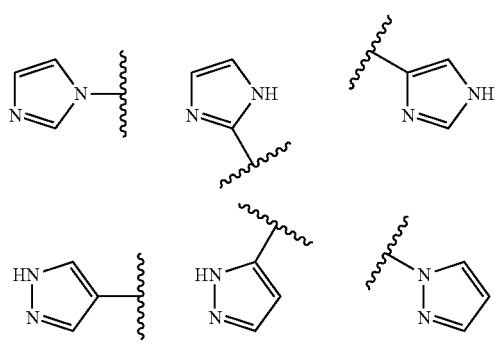

wherein each heteroaryl is substituted or unsubstituted.

In some embodiments, $R^1$ and $R^2$ are the same. In some embodiments, $R^1$ and $R^2$ are different. In some embodiments, at least one of $R^1$ and $R^2$ is a substituted or unsubstituted heteroaryl. For example, the heteroaryl is an N-containing heteroaryl. In some embodiments, the N-containing heteroaryl is an imidazolyl. For example, the N-containing heteroaryl can be selected from the group consisting of:

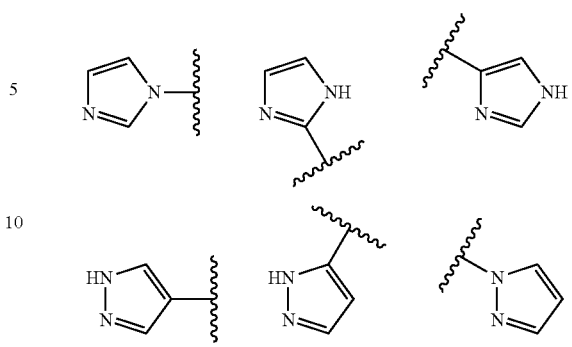

wherein each heteroaryl is substituted or unsubstituted.

Also provided herein is a compound of Formula (II):

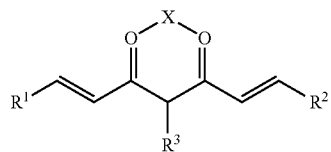

or a pharmaceutically acceptable salt thereof, wherein:

X is absent or selected from the group consisting of: $-CR^4R^5$ and $-BR^4R^5$;

$R^1$ is a substituted or unsubstituted aryl or a substituted or unsubstituted heteroaryl;

$R^2$ is a substituted or unsubstituted aryl or a substituted or unsubstituted heteroaryl;

$R^3$ is H or a $(C_1\text{-}C_6)$alkyl;

$R^4$ and $R^5$ are independently selected from the group consisting of H, halo, and $OR^6$;

$R^6$ is H or a $(C_1\text{-}C_6)$alkyl;

In some embodiments, the compound is other than the following compounds, and salts thereof:

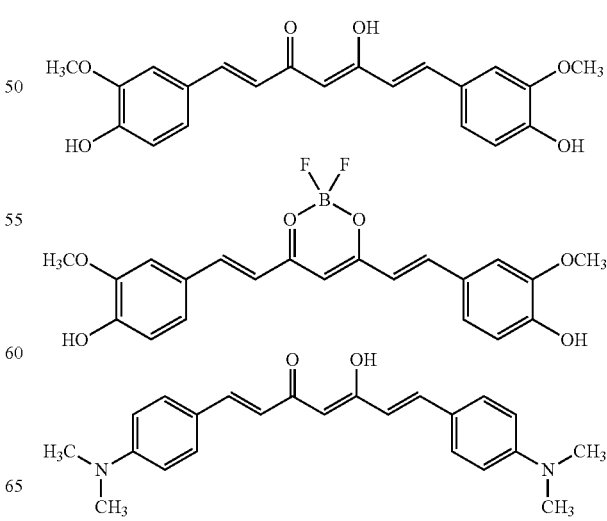

-continued

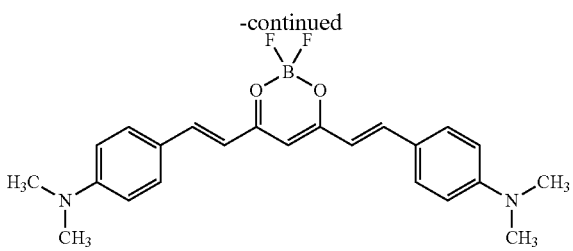

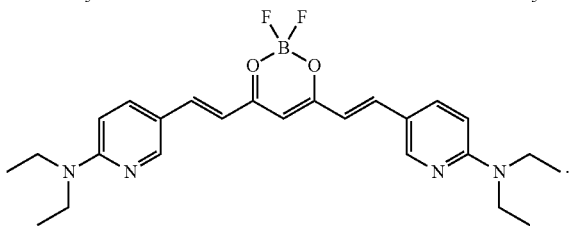

In some embodiments, X is —$BR^4R^5$. For example, $R^4$ and $R^5$ are halo. In some embodiments, $R^4$ and $R^5$ are F. In some embodiments, X is —$CR^4R^5$. For example, in some such embodiments, $R^4$ and $R^5$ are halo. In some embodiments, $R^4$ and $R^5$ are F.

In some embodiments, $R^1$ and $R^2$ are independently:

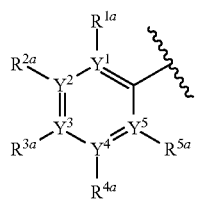

each $Y^1$, $Y^2$, $Y^3$, $Y^4$, and $Y^5$ is independently selected from C and N, wherein no more than two of $Y^1$, $Y^2$, $Y^3$, $Y^4$, and $Y^5$ is N;

$R^{1a}$, $R^{4a}$, and $R^{5a}$ are independently selected from the group consisting of: H, $C_{1-6}$ alkyl, $C_{2-6}$ alkenyl, $C_{2-6}$ alkynyl, halo, $C_{1-6}$ haloalkyl, CN, $NO_2$, $OR^a$, $SR^a$, $C(O)R^a$, $C(O)NR^aR^b$, $C(O)OR^a$, $OC(O)R^a$, $NR^aR^b$, $NR^aC(O)R^b$, $NR^aC(O)OR^b$, $S(O)R^a$, $S(O)_2R^a$, a substituted or unsubstituted aryl, and a substituted or unsubstituted heteroaryl;

$R^{2a}$ is selected from the group consisting of: H, $C_{1-6}$ alkyl, $C_{2-6}$ alkenyl, $C_{2-6}$ alkynyl, halo, $C_{1-6}$ haloalkyl, CN, $NO_2$, $SR^a$, $C(O)R^a$, $C(O)NR^aR^b$, $C(O)OR^a$, $OC(O)R^a$, $NR^aR^b$, $NR^aC(O)R^b$, $NR^aC(O)OR^b$, $S(O)R^a$, $S(O)_2R^a$, a substituted or unsubstituted aryl, and a substituted or unsubstituted heteroaryl;

$R^{3a}$ is selected from the group consisting of: H, $C_{1-6}$ alkyl, $C_{2-6}$ alkenyl, $C_{2-6}$ alkynyl, halo, $C_{1-6}$ haloalkyl, CN, $NO_2$, $SR^a$, $C(O)R^a$, $C(O)NR^aR^b$, $C(O)OR^a$, $OC(O)R^a$, $NR^aC(O)R^b$, $NR^aC(O)OR^b$, $S(O)R^a$, $S(O)_2R^a$, a substituted or unsubstituted aryl, and a substituted or unsubstituted heteroaryl;

each $R^a$ and $R^b$ is independently selected from H, $C_{1-6}$ alkyl, aryl, and heteroaryl; and wherein when any of $Y^1$, $Y^2$, $Y^3$, $Y^4$, or $Y^5$ is N, the corresponding $R^{1a}$, $R^{2a}$, $R^{3a}$, $R^{4a}$, and $R^{5a}$ is absent.

In some embodiments, $Y^4$ is N. In some embodiments, $R^a$ and $R^b$ are independently selected from H and $C_{1-6}$ alkyl.

In some embodiments, $R^1$ and $R^2$ are each independently a substituted aryl. For example, $R^1$ and $R^2$ can be independently:

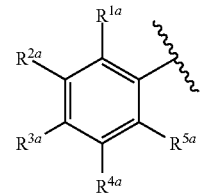

wherein:

$R^{1a}$, $R^{4a}$, and $R^{5a}$ are independently selected from the group consisting of: H, $C_{1-6}$ alkyl, $C_{2-6}$ alkenyl, $C_{2-6}$ alkynyl, halo, $C_{1-6}$ haloalkyl, CN, $NO_2$, $OR^a$, $SR^a$, $C(O)R^a$, $C(O)NR^aR^b$, $C(O)OR^a$, $OC(O)R^a$, $NR^aR^b$, $NR^aC(O)R^b$, $NR^aC(O)OR^b$, $S(O)R^a$, $S(O)_2R^a$, a substituted or unsubstituted aryl, and a substituted or unsubstituted heteroaryl;

$R^{2a}$ is selected from the group consisting of: H, $C_{1-6}$ alkyl, $C_{2-6}$ alkenyl, $C_{2-6}$ alkynyl, halo, $C_{1-6}$ haloalkyl, CN, $NO_2$, $SR^a$, $C(O)R^a$, $C(O)NR^aR^b$, $C(O)OR^a$, $OC(O)R^a$, $NR^aR^b$, $NR^aC(O)R^b$, $NR^aC(O)OR^b$, $S(O)R^a$, $S(O)_2R^a$, a substituted or unsubstituted aryl, and a substituted or unsubstituted heteroaryl;

$R^{3a}$ is selected from the group consisting of: H, $C_{1-6}$ alkyl, $C_{2-6}$ alkenyl, $C_{2-6}$ alkynyl, halo, $C_{1-6}$ haloalkyl, CN, $NO_2$, $SR^a$, $C(O)R^a$, $C(O)NR^aR^b$, $C(O)OR^a$, $OC(O)R^a$, $NR^aC(O)R^b$, $NR^aC(O)OR^b$, $S(O)R^a$, $S(O)_2R^a$, a substituted or unsubstituted aryl, and a substituted or unsubstituted heteroaryl; and each $R^a$ and $R^b$ is independently selected from H, $C_{1-6}$ alkyl, aryl, and heteroaryl.

In some embodiments, $R^a$ and $R^b$ is independently selected from H and $C_{1-6}$ alkyl.

In some embodiments, $R^{3a}$ is a substituted or unsubstituted heteroaryl. In some embodiments, $R^{3a}$ is a substituted or unsubstituted N-containing heteroaryl. For example, the N-containing heteroaryl can be an imidazolyl. Non-limiting examples of imidazolyls and pyrazolyls include:

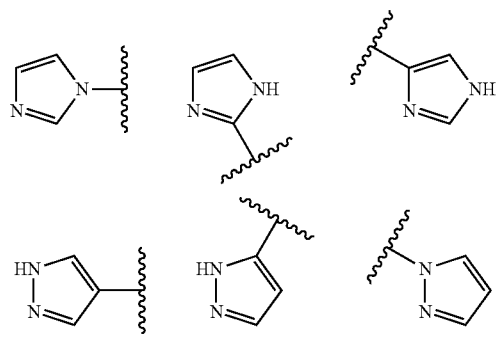

wherein each heteroaryl is substituted or unsubstituted.

In some embodiments, $R^1$ and $R^2$ are the same. In some embodiments, $R^1$ and $R^2$ are different. In some embodiments, at least one of $R^1$ and $R^2$ is a substituted or unsubstituted heteroaryl. For example, the heteroaryl is an N-containing heteroaryl. In some embodiments, the N-containing heteroaryl is an imidazolyl. For example, the N-containing heteroaryl can be selected from the group consisting of:

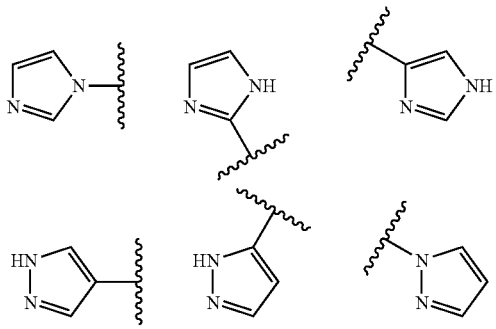

wherein each heteroaryl is substituted or unsubstituted.

Further provided herein is a compound of Formula (III)

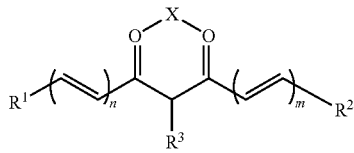

or a pharmaceutically acceptable salt thereof,
wherein:
X is absent or selected from the group consisting of: —$CR^4R^5$ and —$BR^4R^5$;
$R^1$ is a substituted or unsubstituted aryl or a substituted or unsubstituted heteroaryl;
$R^2$ is a substituted or unsubstituted aryl or a substituted or unsubstituted heteroaryl;
$R^3$ is H or a $(C_1-C_6)$alkyl;
$R^4$ and $R^5$ are independently selected from the group consisting of H, halo, and $OR^6$;
$R^6$ is H or a $(C_1-C_6)$alkyl;
n and m are independently integers from 0-2, wherein at least one of n or m is not 0; and
wherein $R^1$ and $R^2$ are different.

In some embodiments, X is —$BR^4R^5$. For example, $R^4$ and $R^5$ are halo. In some embodiments, $R^4$ and $R^5$ are F. In some embodiments, X is —$CR^4R^5$. For example, in some such embodiments, $R^4$ and $R^5$ are halo. In some embodiments, $R^4$ and $R^5$ are F. In some embodiments, X is absent. In some embodiments, n and m are each 1. In some embodiments, n is 0 and m is 1 or 2. In some embodiments, n is 1 and m is 2.

In some embodiments, $R^1$ and $R^2$ are independently:

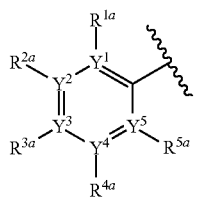

each $Y^1$, $Y^2$, $Y^3$, $Y^4$, and $Y^5$ is independently selected from C and N, wherein no more than two of $Y^1$, $Y^2$, $Y^3$, $Y^4$, and $Y^5$ is N;
$R^{1a}$, $R^{4a}$, and $R^{5a}$ are independently selected from the group consisting of: H, $C_{1-6}$ alkyl, $C_{2-6}$ alkenyl, $C_{2-6}$ alkynyl, halo, $C_{1-6}$ haloalkyl, CN, $NO_2$, $OR^a$, $SR^a$, $C(O)R^a$, $C(O)NR^aR^b$, $C(O)OR^a$, $OC(O)R^a$, $NR^aR^b$, $NR^aC(O)R^b$, $NR^aC(O)OR^b$, $S(O)R^a$, $S(O)_2R^a$, a substituted or unsubstituted aryl, and a substituted or unsubstituted heteroaryl;
$R^{2a}$ is selected from the group consisting of: H, $C_{1-6}$ alkyl, $C_{2-6}$ alkenyl, $C_{2-6}$ alkynyl, halo, $C_{1-6}$ haloalkyl, CN, $NO_2$, $SR^a$, $C(O)R^a$, $C(O)NR^aR^b$, $C(O)OR^a$, $OC(O)R^a$, $NR^aR^b$, $NR^aC(O)R^b$, $NR^aC(O)OR^b$, $S(O)R^a$, $S(O)_2R^a$, a substituted or unsubstituted aryl, and a substituted or unsubstituted heteroaryl;
$R^{3a}$ is selected from the group consisting of: H, $C_{1-6}$ alkyl, $C_{2-6}$ alkenyl, $C_{2-6}$ alkynyl, halo, $C_{1-6}$ haloalkyl, CN, $NO_2$, $SR^a$, $C(O)R^a$, $C(O)NR^aR^b$, $C(O)OR^a$, $OC(O)R^a$, $NR^aC(O)R^b$, $NR^aC(O)OR^b$, $S(O)R^a$, $S(O)_2R^a$, a substituted or unsubstituted aryl, and a substituted or unsubstituted heteroaryl;
each $R^a$ and $R^b$ is independently selected from H, $C_{1-6}$ alkyl, aryl, and heteroaryl; and
wherein when any of $Y^1$, $Y^2$, $Y^3$, $Y^4$, or $Y^5$ is N, the corresponding $R^{1a}$, $R^{2a}$, $R^{1a}$, $R^{4a}$, and $R^{5a}$ is absent.

In some embodiments, $Y^4$ is N. In some embodiments, $R^a$ and $R^b$ are independently selected from H and $C_{1-6}$ alkyl.

In some embodiments, $R^1$ and $R^2$ are each independently a substituted aryl. For example, $R^1$ and $R^2$ can be independently:

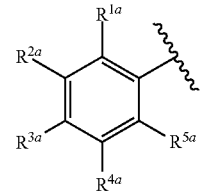

wherein:
$R^{1a}$, $R^{4a}$, and $R^{5a}$ are independently selected from the group consisting of: H, $C_{1-6}$ alkyl, $C_{2-6}$ alkenyl, $C_{2-6}$ alkynyl, halo, $C_{1-6}$ haloalkyl, CN, $NO_2$, $OR^a$, $SR^a$, $C(O)R^a$, $C(O)NR^aR^b$, $C(O)OR^a$, $OC(O)R^a$, $NR^aR^b$, $NR^aC(O)R^b$, $NR^aC(O)OR^b$, $S(O)R^a$, $S(O)_2R^a$, a substituted or unsubstituted aryl, and a substituted or unsubstituted heteroaryl;
$R^{2a}$ is selected from the group consisting of: H, $C_{1-6}$ alkyl, $C_{2-6}$ alkenyl, $C_{2-6}$ alkynyl, halo, $C_{1-6}$ haloalkyl, CN, $NO_2$, $SR^a$, $C(O)R^a$, $C(O)NR^aR^b$, $C(O)OR^a$, $OC(O)R^a$, $NR^aR^b$, $NR^aC(O)R^b$, $NR^aC(O)OR^b$, $S(O)R^a$, $S(O)_2R^a$, a substituted or unsubstituted aryl, and a substituted or unsubstituted heteroaryl;
$R^{3a}$ is selected from the group consisting of: H, $C_{1-6}$ alkyl, $C_{2-6}$ alkenyl, $C_{2-6}$ alkynyl, halo, $C_{1-6}$ haloalkyl, CN, $NO_2$, $SR^a$, $C(O)R^a$, $C(O)NR^aR^b$, $C(O)OR^a$, $OC(O)R^a$, $NR^aC(O)R^b$, $NR^aC(O)OR^b$, $S(O)R^a$, $S(O)_2R^a$, a substituted or unsubstituted aryl, and a substituted or unsubstituted heteroaryl; and
each $R^a$ and $R^b$ is independently selected from H, $C_{1-6}$ alkyl, aryl, and heteroaryl.

In some embodiments, $R^a$ and $R^b$ is independently selected from H and $C_{1-6}$ alkyl.

In some embodiments, $R^{3a}$ is a substituted or unsubstituted heteroaryl. In some embodiments, $R^{3a}$ is a substituted or unsubstituted N-containing heteroaryl. For example, the N-containing heteroaryl can be an imidazolyl. Non-limiting examples of imidazolyls and pyrazolyls include:

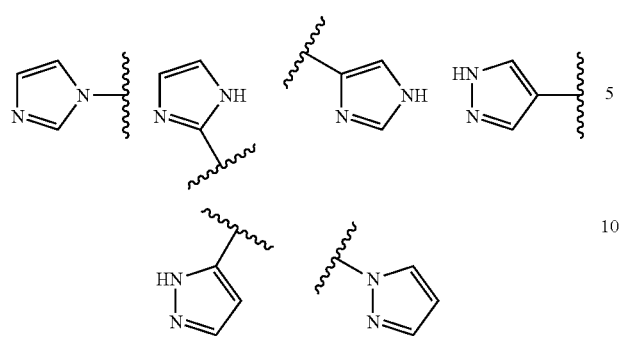

wherein each heteroaryl is substituted or unsubstituted.

In some embodiments, at least one of $R^1$ and $R^2$ is a substituted or unsubstituted heteroaryl. For example, the heteroaryl is an N-containing heteroaryl. In some embodiments, the N-containing heteroaryl is an imidazolyl. For example, the N-containing heteroaryl can be selected from the group consisting of:

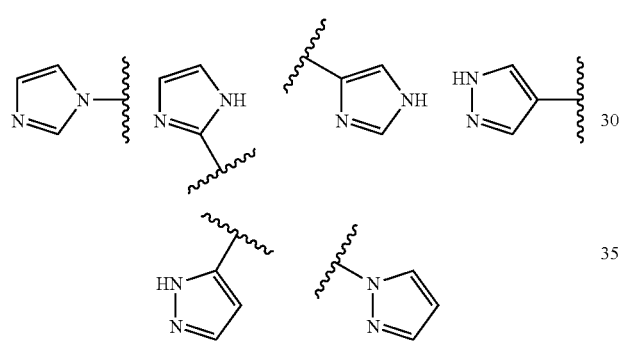

wherein each heteroaryl is substituted or unsubstituted.

Non-limiting examples of a compound of Formula (I), (II), and/or (III) include:

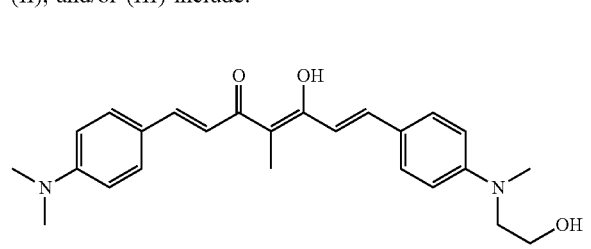

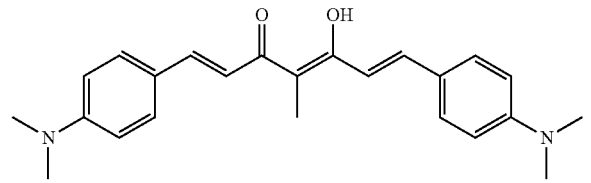

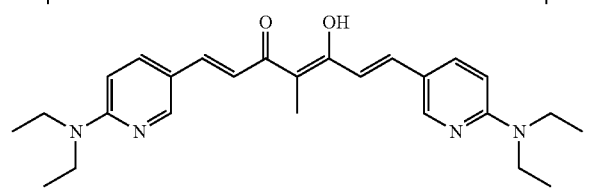

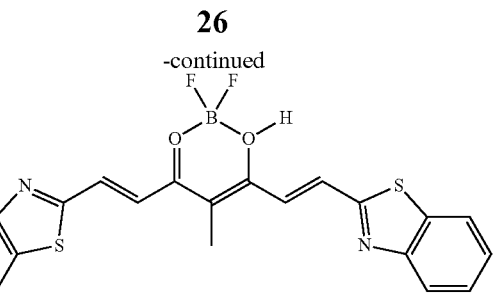

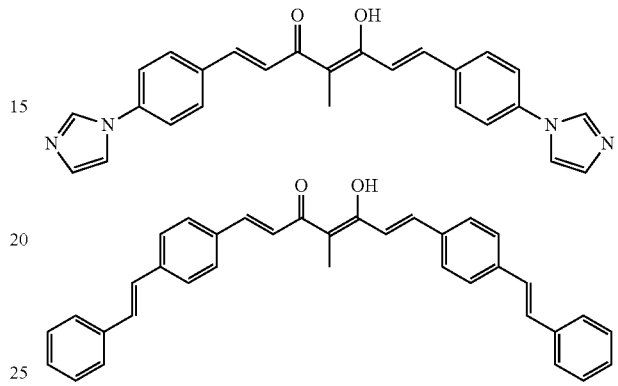

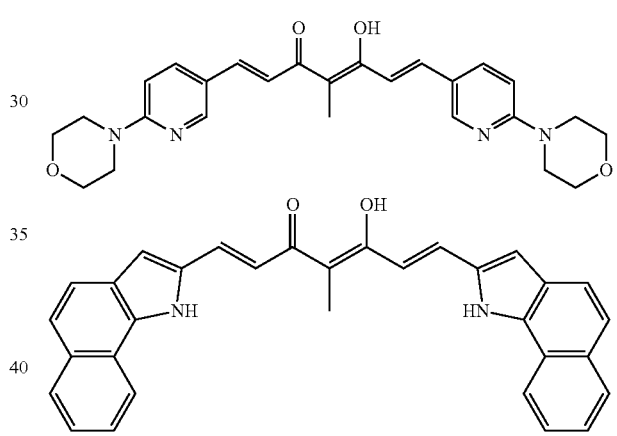

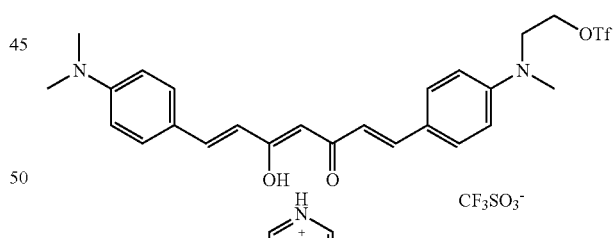

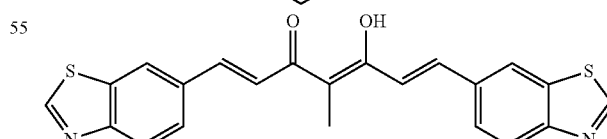

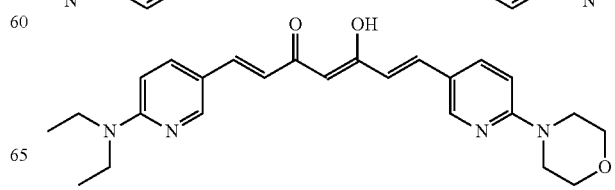

27
-continued
28
-continued
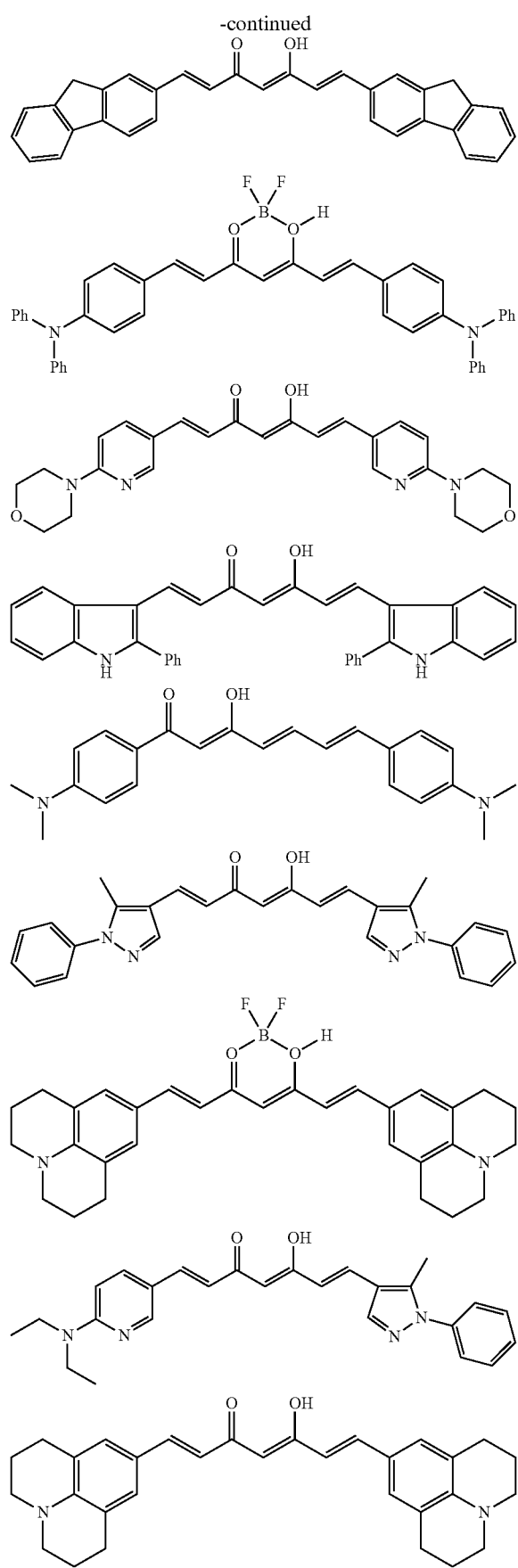
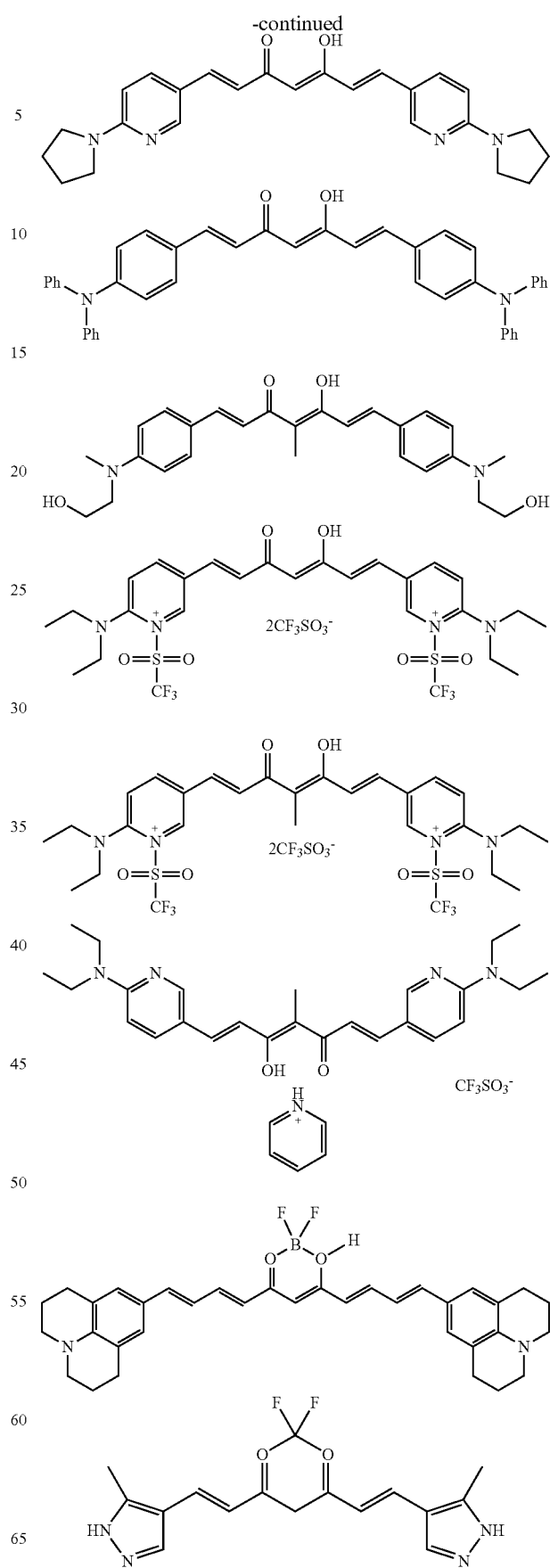

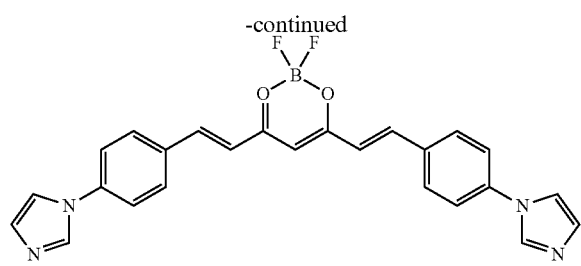

or a pharmaceutically acceptable salt form thereof.

In some embodiments, a compound of Formula (I) (e.g., a compound of Formula (II) or (III)) is selected from the group consisting of:

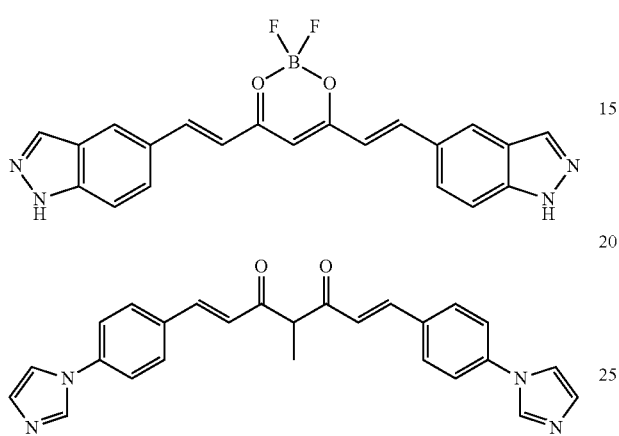

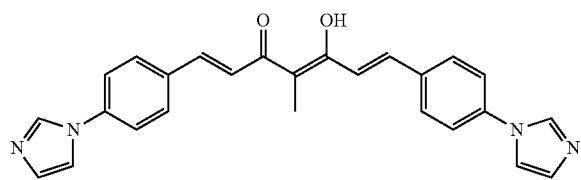

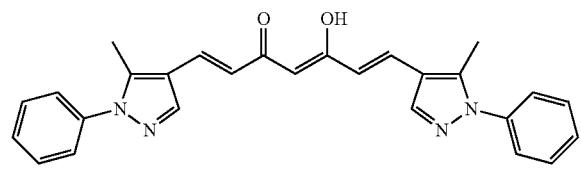

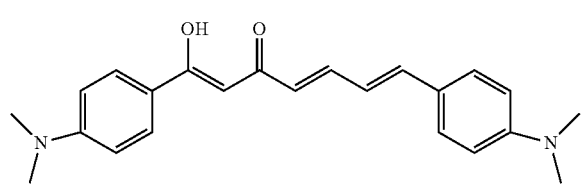

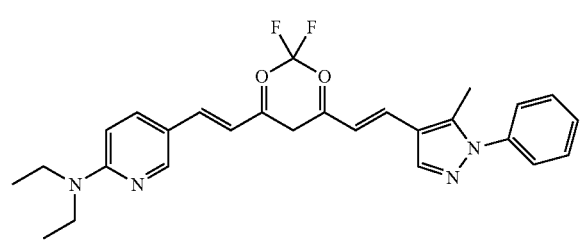

or a pharmaceutically acceptable salt thereof.

Pharmaceutical Compositions and Methods of Administration

Provided herein is the manufacture and use of pharmaceutical compositions, which include one or more compounds described herein.

Pharmaceutical compositions typically include a pharmaceutically acceptable carrier. As used herein the language "pharmaceutically acceptable carrier" includes saline, solvents, dispersion media, coatings, antibacterial and antifungal agents, isotonic and absorption delaying agents, and the like, compatible with pharmaceutical administration. Supplementary compounds can also be incorporated into the compositions, e.g., compounds that aid in the transportation of a compound as provided herein (e.g., a compound of Formula (I), (II), and/or (III)) across the blood-brain barrier (BBB). In some embodiments, the compounds provided herein may be conjugated or formulated to aid in their transportation across the BBB. Such methods are known in the art.

Pharmaceutical compositions are typically formulated to be compatible with its intended route of administration. Examples of routes of administration include parenteral, e.g., intravenous, oral (e.g., inhalation), and transmucosal (e.g., intranasal).

Methods of formulating suitable pharmaceutical compositions are known in the art, see, e.g., *Remington: The Science and Practice of Pharmacy*, 21st ed., 2005; and the books in the series *Drugs and the Pharmaceutical Sciences: a Series of Textbooks and Monographs* (Dekker, N.Y.). For example, solutions or suspensions used for parenteral administration can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use can include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent that delays absorption, for example, aluminum monostearate and gelatin.

Sterile injectable solutions can be prepared by incorporating a compound as provided herein in the required amount in an appropriate solvent with one or a combination of ingredients enumerated above, as required, followed by filtered sterilization. Generally, dispersions are prepared by incorporating the compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yield a powder of the compound plus any additional desired ingredient from a previously sterile-filtered solution thereof.

Oral compositions generally include an inert diluent or an edible carrier. For the purpose of oral therapeutic administration, a compound as provided herein can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds can be delivered in the form of an aerosol spray from a pressured container or dispenser that contains a suitable propellant, e.g., a gas such as carbon dioxide, or a nebulizer. Such methods include those described in U.S. Pat. No. 6,468,798.

Systemic administration of a therapeutic compound as described herein can also be by transmucosal (e.g., intranasal) means. For transmucosal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For example, intranasal delivery is possible, as described in, inter alia, Hamajima et al., Clin. Immunol. Immunopathol., 88(2), 205-10 (1998). Liposomes (e.g., as described in U.S. Pat. No. 6,472,375) and microencapsulation can also be used. Biodegradable targetable microparticle delivery systems can also be used (e.g., as described in U.S. Pat. No. 6,471,996).

In one embodiment, the compounds as provided herein are prepared with carriers that will protect the therapeutic compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques, or obtained commercially, e.g., from Alza Corporation and Nova Pharmaceuticals, Inc. Liposomal suspensions (including liposomes targeted to selected cells with monoclonal antibodies to cellular antigens) can also be used as pharmaceutically acceptable carriers. These can be prepared according to methods known to those skilled in the art, for example, as described in U.S. Pat. No. 4,522,811.

The pharmaceutical compositions can be included in a container, pack, or dispenser together with instructions for administration. An "effective amount" is an amount sufficient to effect beneficial or desired results. For example, a therapeutic amount is one that achieves the desired therapeutic effect. This amount can be the same or different from a prophylactically effective amount, which is an amount necessary to prevent onset of disease or disease symptoms. An effective amount can be administered in one or more administrations, applications or dosages. A therapeutically effective amount of a therapeutic compound (i.e., an effective dosage) depends on the therapeutic compounds selected. The compositions can be administered one from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the therapeutic compounds described herein can include a single treatment or a series of treatments.

Dosage, toxicity and therapeutic efficacy of the therapeutic compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

Methods of Treatment

The methods described herein include methods for the treatment of disorders associated with amyloid β plaque formation. In some embodiments, the disorder is Alzheimer's Disease or a related disorder. Generally, the methods include administering a therapeutically effective amount of a compound as described herein, to a patient who is in need of, or who has been determined to be in need of, such treatment.

As used in this context, to "treat" means to ameliorate at least one symptom of the disorder associated with Alzehimer's Disease. Often, Alzheimer's Disease results in loss of memory, disorientation and misinterpreting special relationships, difficulty speaking and writing, trouble concentrating, thinking, and/or reasoning, difficulty making judgments or decisions, trouble planning and performing familiar tasks (e.g., cooking a meal, playing a favorite game, or dressing and bathing), and changes in personality and behavior (e.g., depression, social withdrawal, mood swings, distrust in others, irritability and aggressiveness, changes in sleeping habits, wandering, loss of inhibitions, and/or delusions); thus, a treatment can result in a reduction in one or more of these symptoms. Administration of a therapeutically effective amount of a compound provided herein for the treatment of a condition associated with amyloid β plaque formation will result in increased mental function and neuronal protection.

In some embodiments, the methods provided herein can be used to treat an Alzheimer's Disease (AD) related disorder. The term "AD related disorder" includes senile dementia of AD type (SDAT), Parkinson's disease, Lewis body dementia, vascular dementia, mild cognitive impairment (MCI), age-associated memory impairment (AAMI) and problems associated with ageing, post-encephalitic Parkinsonism, Amyotrophic lateral sclerosis (ALS), multiple sclerosis (MS) and Down syndrome.

A method of binding amyloid β (Aβ) in a cell is also provided herein, the method comprising contacting the cell with an effective amount of a compound provided herein. In some embodiments, the binding or interaction with Aβ results in the attenuation of copper-induced crosslinking of Aβ. The method of binding Aβ in a cell may be performed by contacting the cell with a compound provided herein, or a pharmaceutically acceptable salt form thereof, in vitro, thereby inducing binding of Aβ in a cell in vitro. Uses of such an in vitro methods of binding Aβ include, but are not limited to use in a screening assay (for example, wherein a compound provided herein is used as a positive control or standard compared to compounds of unknown activity or potency in binding Aβ). In some embodiments thereof, binding of Aβ is performed in a brain cell.

The method of binding Aβ in a cell may be performed, for example, by contacting a brain cell with a compound provided herein, in vivo, thereby binding Aβ in a patient in vivo. The contacting is achieved by causing a compound as provided herein, or a pharmaceutically acceptable salt form thereof, to be present in the patient in an amount effective to achieve binding of Aβ. This may be achieved, for example, by administering an effective amount of a compound provided herein, or a pharmaceutically acceptable salt form thereof, to a patient. Uses of such an in vivo methods of binding Aβ include, but are not limited to, use in methods of treating a disease or condition, wherein binding Aβ is beneficial. In some embodiments thereof, binding of Aβ results in attenuation of copper-induced crosslinking of Aβ in a brain cell, for example in a patient suffering from Alzheimer's Disease or a related disorder. The method is preferably performed by administering a therapeutically effective amount of a compound provided herein, or a pharmaceutically acceptable salt form thereof, to a patient who is suffering from Alzheimer's Disease or a related disorder.

EXAMPLES

The invention is further described in the following examples, which do not limit the scope of the invention described in the claims.

General Methods

Reagents used for the synthesis were purchased from Aldrich and used without further purification. Column chromatography was performed on silica gel (SiliCycle Inc., 60 Å, 40-63 mm) slurry packed into glass columns. Synthetic amyloid-β peptide (1-40/42) was purchased from rPeptide (Bogart, Ga., 30622). FAM-Aβ42 and [H13R] Aβ40 were purchased from American Peptide Company. Aggregates for in vitro studies were generated by slow stirring of Aβ40 (25 μM) in PBS buffer for 3 days at room temperature. The Aβ peptide fragments (KLVFF) were purchased from CS Bio Co. All compounds were dissolved in DMSO to make 2.5 mM stock solutions to be used in further experiments. $^1$H and $^{13}$C NMR spectra were recorded at 500 MHz and 125 MHz respectively, and reported in ppm downfield from tetramethylsilane. Fluorescence studies were carried out using a F-4500 Fluorescence Spectrophotometer. Mass spectra were carried out using Hewlett Packard Series 1100 MSD. Novex® Tris-Glycine gels, running and loading buffers, membranes, and other reagents were purchased from Invitrogen.

Example 1

Synthesis of CRANAD-17

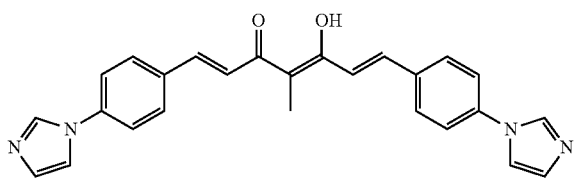 [SMILES: C/C(C(=O)/C=C/c1ccc(-n2ccnc2)cc1)=C(O)\C=C\c1ccc(-n2ccnc2)cc1]

The synthesis of intermediate materials (2,2-difluro-1,3-dioxaboryl-3-pentadione) were performed using a modified procedure (Ran C, et al., *J Am Chem Soc* 2009; 131:15257-

61). The above intermediate compound (80 mg, 0.5 mmol) was dissolved in acetonitrile (4.0 mL), followed by the addition of acetic acid (0.1 mL), tetrahydroisoquinoline (20 uL), and 4-(1H-Imidazol-1-yl)benzaldehyde (172 mg, 1 mmol). The resulting solution was stirred at 60° C. for 4 hours. An orange solid was obtained after filtrating the reaction mixture and the solid was washed with EtOAc to give a dark orange powder CRANAD-17, 46 mg, yield 20%. $^1$H NMR (DMSO-d6) δ(ppm) 6.63(S, 1H), 7.14(S, 2H), 7.31 (d, 2H, J=15.5 Hz), 7.82 (d, 4H, J=8.5 Hz), 7.88 (s, 2H), 8.03 (d, 4H, J=8.5 Hz), 8.08 (d, 2H, J=15.5 Hz), 8.43 (s, 2H); $^{13}$C NMR (DMSO-d6) δ(ppm) 102.99, 118.15, 120.73, 121.98, 130.71, 131.79, 132.82, 136.10, 139.60, 146.15, 180.35; $^{19}$F NMR (DMSO-d6) δ(ppm) 137.069, 137.129; ESI-MS (M−H) m/z=458.2.

Example 2

Synthesis of CRANAD-27

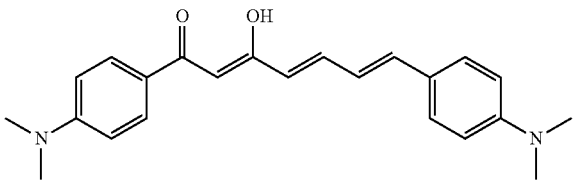

The synthesis of intermediate materials (1-(4-(Dimethylamino)phenyl)-4,4-dimethyl-1,3-pentanedione) were performed according to reference (Popic, V. V. et al. *Synthesis* 1991, (3), 195-8). Then boric oxide (34 mg, 0.5 mmol) was dissolved in DMF (1 mL) at 120° C. To this solution, the above intermediate compound (102 mg, 0.5 mmol) was added, followed by tributyl borate (0.27 mL 2 mmol) at 120° C. and stirred for 5 min. To the borate complex, 4-dimethylaminocinnamaldehyde (88 mg, 0.5 mmol) was added and stirred for 5 min. A mixture of 1,2,3,4-tetrahydroquinoline (10 uL) and acetic acid (30 uL) in DMF (1 mL) was added to the reaction mixture and heated to 120° C. for 2 h. After cooling to room temperature, the reaction mixture was poured into ice-water and a reddish precipitate was collected. The precipitate was further purified by silica gel column using ethyl acetate/hexanes (1:8) as an eluent to give a reddish powder of CRANAD-27 (16 mg, yield: 8.8%). $^1$H NMR (CDCl$_3$) δ(ppm) 3.01 (s, 6H), 3.06 (s, 6H), 6.08 (d, 1H, J=15.0 Hz), 6.15 (s, 1H), 6.67-6.83 (m, 6H), 7.36-7.46 (m, 3H), 7.86 (d, 2H, J=9.0 Hz); $^{13}$C NMR (CDCl$_3$) δ(ppm) 40.0, 40.2, 96.1, 110.9, 112.1, 123.0, 123.9, 124.5, 128.5, 129.3, 139.7, 140.0, 153.1, 177.4, 188.6; ESI-MS (M+H) m/z=363.3

Example 3

Synthesis of CRANAD-30

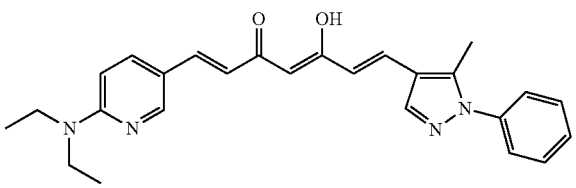 [SMILES: CCN(CC)c1ccc(/C=C/C(=O)/C=C(O)/C=C/c2cnn(-c3ccccc3)c2C)cn1]

Synthesis followed the similar procedure as for CRANAD-17. Gained CRANAD-30 as a dark purple powder, yield: 41.9% $^1$H NMR (CDCl$_3$) δ(ppm) 1.23 (t, 6H, J=7.0 Hz), 2.46 (s, 3H), 3.60 (q, 4H, J=7.0 Hz), 5.85 (s, 1H), 6.36-6.46 (m, 3H), 7.35-7.39 (m, 3H), 7.42-7.45 (m, 2H), 7.62 (dd, 1H, J=2.5, 9.0 Hz), 7.83-7.90 (m, 3H), 8.28 (d, 1H, J=2.5 Hz); $^{13}$C NMR (CDCl$_3$) δ(ppm) 11.0, 12.9, 43.1, 101.1, 106.2, 114.7, 117.92, 117.99, 118.1, 125.0, 128.5, 129.3, 135.7, 136.1, 138.8, 139.0, 141.2, 145.3, 153.2, 177.8, 179.1; $^{19}$F NMR (CDCl$_3$) δ(ppm) 141.57, 141.63; ESI-MS (M$^+$) m/z=477.2 .

Example 4

Fluorescence Spectra Recording

The procedure described below was used for all experiments. To test the interactions of CRANAD-17 with Aβ species including Aβ42 monomers, Aβ40 monomers and [H13R]Aβ40 monomers, we utilize the following protocol. Step 1: 1.0 mL of PBS buffer was added to a quartz curvet as a blank control and its fluorescence was recorded with the same parameters as for CRANAD-17; Step 2: fluorescence of a CRANAD-17 solution (1 mL, 500 nM) was recorded with excitation at 480 nm and emission from 500 nm to 900 nm; Step 3: to the above CRANAD-17 solution, 10 μL of Aβ species (25 μM) was added to make the final Aβ species concentration of 250 nM, and the fluorescence spectrum from this solution was recorded. The final spectra from steps 2 and 3 were corrected using the blank control from step 1.

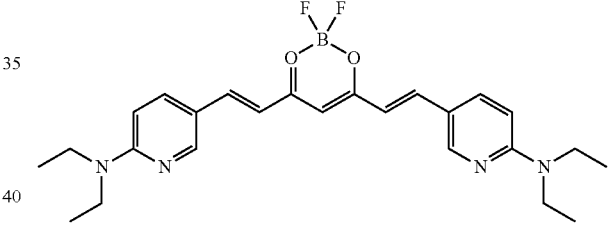

CRANAD-3

Figure 2A:
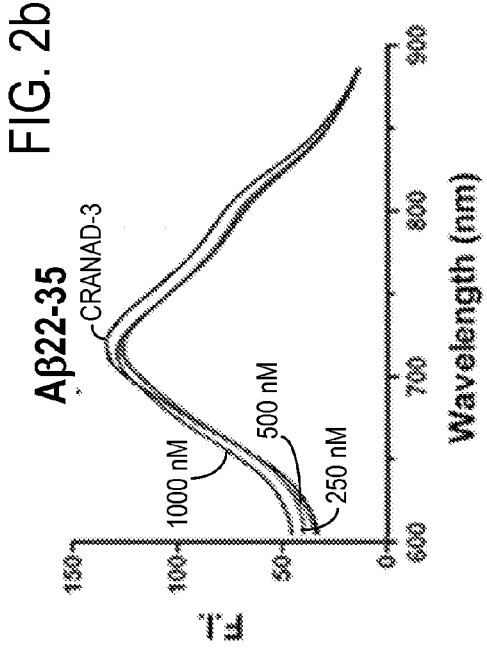
FIG. 2 illustrates the fluorescence spectra of CRANAD-3 with Aβ16-20 (a), Aβ22-35 (b), acetylated Aβ16-20 (c); and Amylin 20-29 (d).

The interaction of CRANAD-3 with various Aβ species has been previously demonstrated (Ran C. and Moore A. *Molecular Imaging and Biology* 14(3): 293-300 (2012)). To further investigate the interaction mechanism, an effort was made to identify the segment within the peptide that was essential for the binding. The segment Aβ16-20 (KLVFF) has the highest hydrophobicity within the peptide and is widely considered as the core segment for aggregation process. The probe was first tested with this segment. To exclude possible response from its aggregated form, the non-aggregating morphology of Aβ16-20 was confirmed by TEM. Upon incubation with this segment, CRANAD-3 displayed a significant fluorescence intensity (F.I.) increase (25%-50% increase in the concentration rage of 250-1000 nM of the peptide), and a 6 nm emission blue-shift, indicating that the probe had specific interaction with the KLVFF segment FIG. 2a.

Figure 2B:
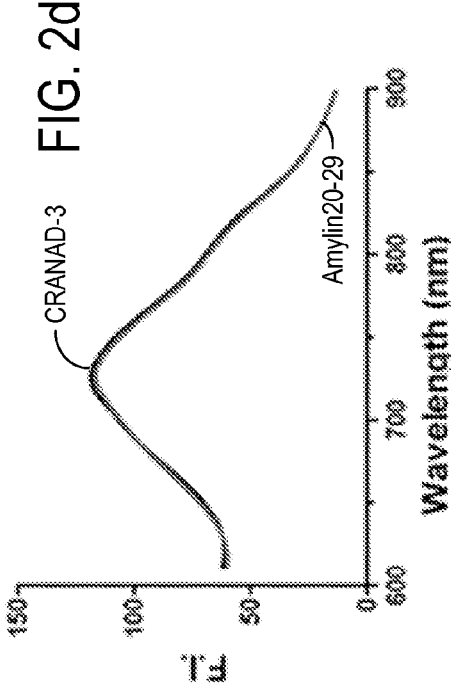

To further confirm that the fluorescence property changes originated from KLVFF segment, CRANAD-3 was tested with non-KLVFF containing peptide Aβ22-35. No significant change in fluorescence intensity was observed with this peptide (FIG. 2b). Based on the above results, it was concluded that the KLVFF fragment was most likely the core structure for the observed interaction.

Figure 2C:
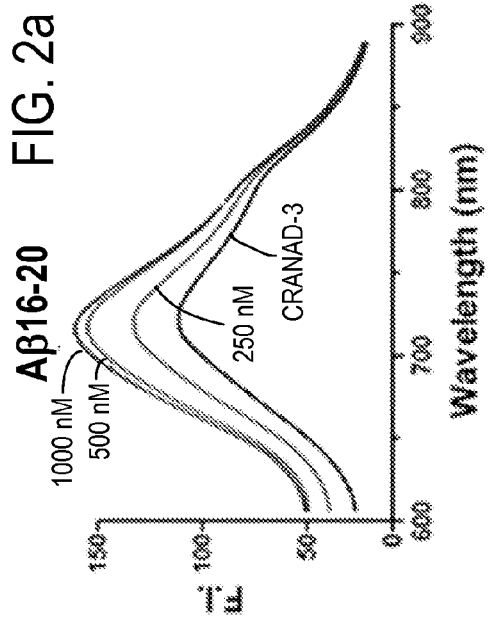
Figure 2D:
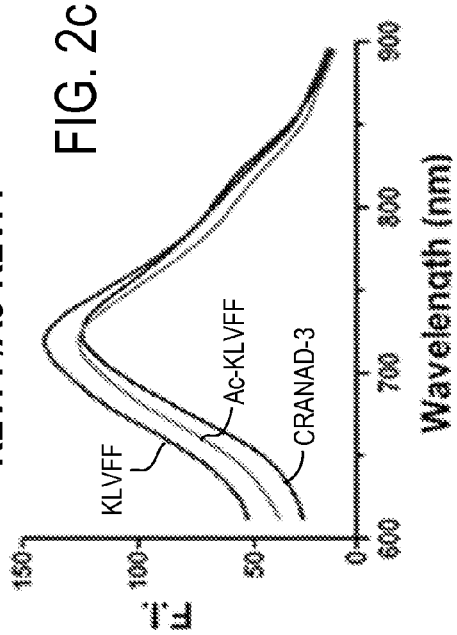

It has been reported that Lysine 16 (K16) in the core peptide is a hot spot for atheronal-induced fibrillization of Aβ. To test whether K16 could also be a hot spot for the interaction between CRANAD-3 and Aβ peptide, the ε-amino group of lysine within the KLVFF fragment was blocked by acetylation. The F.I. of CRANAD-3 with acetylated KLVFF was significantly lower than that with unmodified KLVFF (FIG. 2c). Interestingly, it was found that there was a small blue-shift (5 nm) in the CRANAD-3 emission spectrum upon interaction with the acetylated KLVFF fragment (FIG. 2c), suggesting the existence of a hydrophobic interaction between CRANAD-3 and hydrophobic VFF motif. These results indicated that K16 is important to the interaction of the peptide with CRANAD-3. In addition, CRANAD-3 was also tested with the core fragment of Amylin (Amylin 20-29), an aggregating-prone 37-amino acid peptide, and no significant fluorescence property change was observed (FIG. 2d).

Figure 3A:
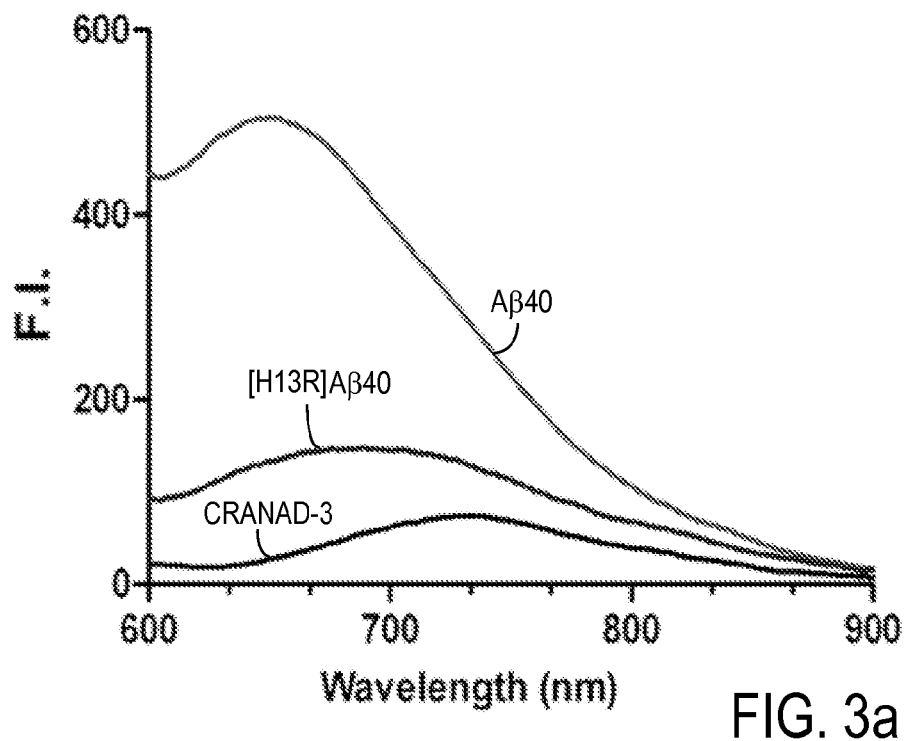
FIG. 3a is a fluorescence spectra of CRANAD-3 alone (black) and with human Aβ340 (red; top), and [H13R]Aβ[40 (blue; middle).

CRANAD-3 is a symmetric compound, and the above data indicate that the aromatic ring on one end is involved in specific interaction with the VFF segment, while the boron-diketone moiety probably binds to ε-NH2 of K16. Conceivably, it is possible that the pyridyl ring on the other end of CRANAD-3 has a specific interaction with H13 and H14 of Aβ, which have aromatic imidazolium rings and are at the equal distance from K16 as VFF. To this end, the fluorescence intensities of CRANAD-3 with Aβ and H13R substituted Aβ ([H13R]Aβ), in which H13 is replaced by arginine (R) was compared. A significantly lower fluorescence intensity was observed for [H13R]Aβ, suggesting that CRANAD-3 specifically interacts with H13 (FIG. 3a).

It has been reported that copper could coordinate with two imidazoles on H13 and H14 of Aβ to induce crosslinking at tyrosine position. A curcumin analogue CRANAD-17 (FIG. 3b) was designed, in which a curcumin scaffold was used as an anchoring moiety to usher the designed compound to the vicinity of H13 and H14 of Aβ, and an imidazolium ring was introduced into the structure to compete with H13/H14 for copper binding sites.

Figure 3B:
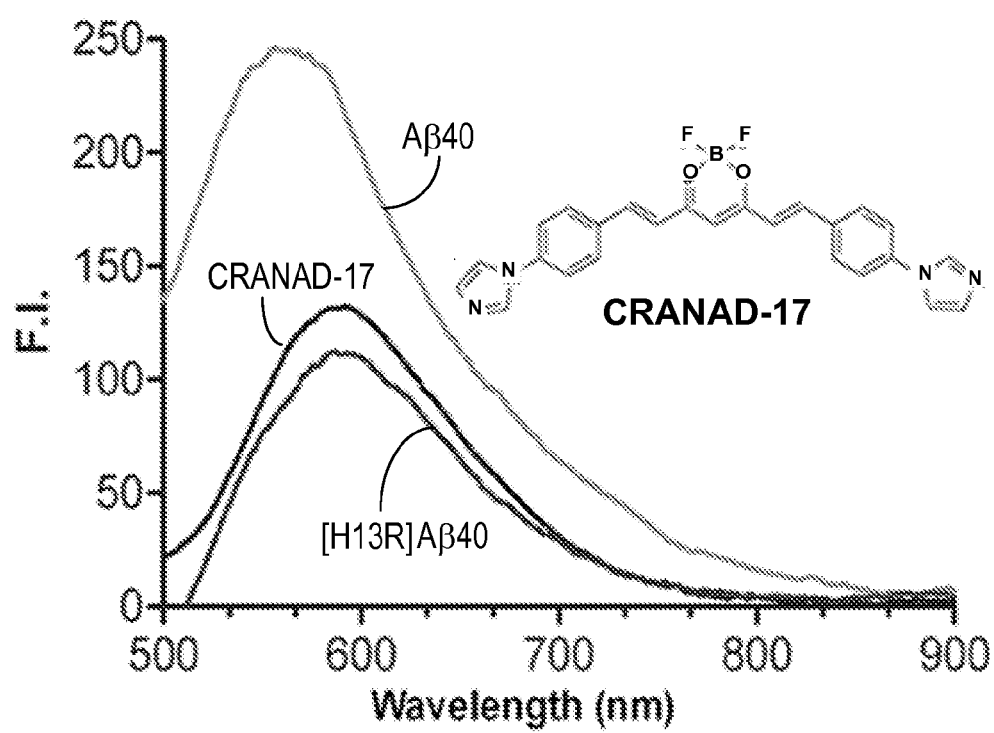
FIG. 3b is a fluorescence spectra of CRANAD-17 alone (black; middle), with human Aβ40 (red; top), and with [H13R]Aβ40 (blue; bottom).

Similar to CRANAD-3, upon mixing with Aβ, CRANAD-17 displayed fluorescence property changes resulted in intensity increase and blue-shift, indicating that this compound could be specific towards Aβ (red line, FIG. 3b). However, significantly lower fluorescence intensity and no significant blue-shift upon CRANAD-17 incubation with [H13R]Aβ was observed compared to native Aβ (blue line, FIG. 3b), suggesting that CRANAD-17 specifically interacts with H13 within Aβ.

Example 5

NMR Studies with KLVFF Segment

A $^1$H NMR spectrum of DMSO-d6 solution of KLVFF (2.0 mM) was recorded at 300° C. followed by addition of 0.96 mg CRANAD-3 (2.0 mM). The resulting solution was kept at room temperature overnight, and then subjected to $^1$H NMR spectrum recording at 300° C. Similar procedure was used for CRANAD-17. The ppm reference peaks were set at 2.49 ppm with DMSO-d6 as the reference.

Figure 4:
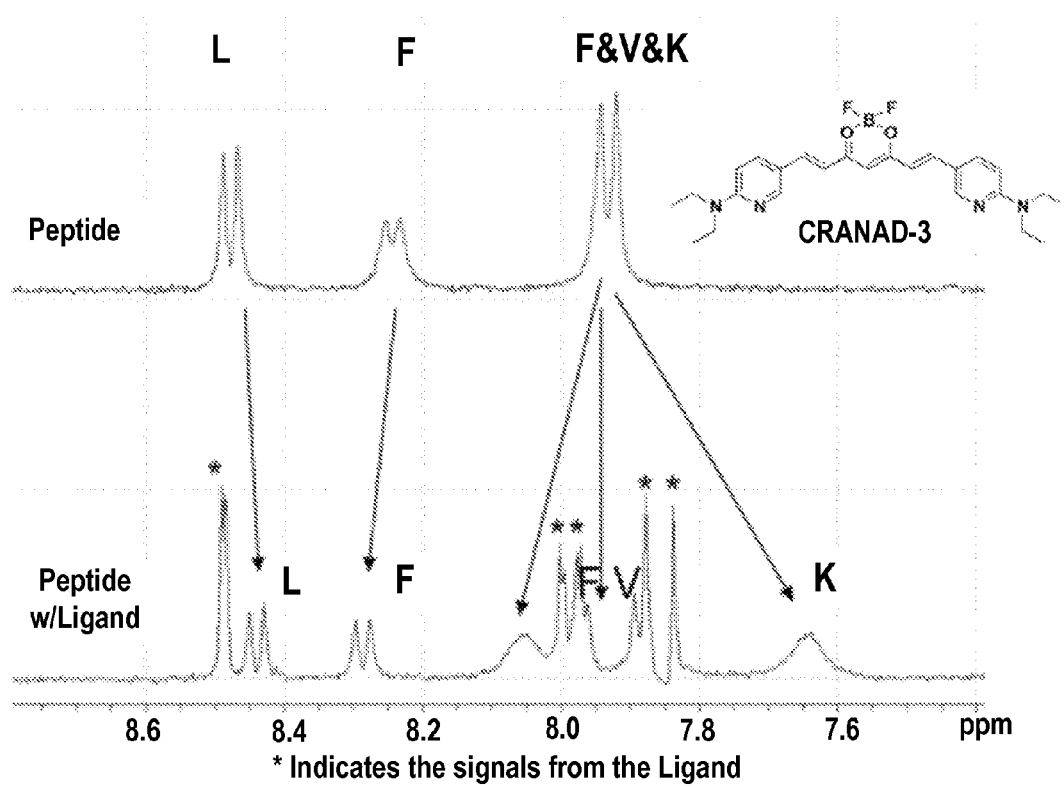
FIG. 4 provides a $^1$H NMR spectra of KLVFF (top) and of KLVFF with CRNAD-3 (bottom). * indicated that the peaks originated from CRANAD-3.
Figure 5:
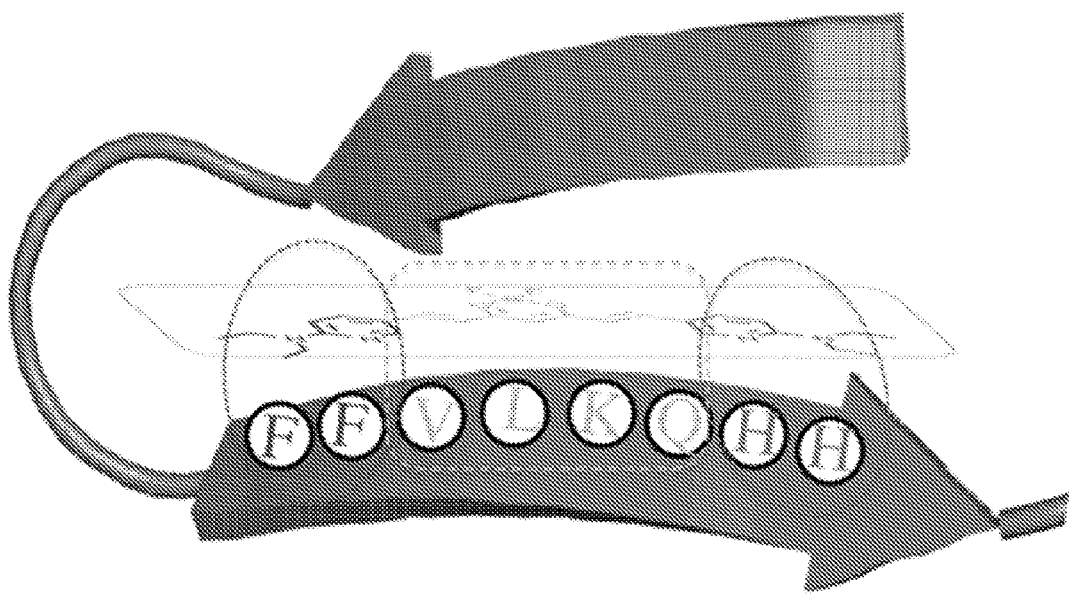
FIG. 5 illustrates the proposed interaction model of CRANAD-3 with Aβ40/42, in which the three interacting pockets are highlighted with circles or rectangle.

The interaction between CRANAD-3 and the KLVFF fragment was confirmed with NMR spectroscopy, in which signals from amide protons of K, V, F were significantly shifted (FIG. 4). Particularly, where the spectrum was very broad with no visible peaks, the exchangeable proton peaks of K16 were remarkably sharper in the presence of CRANAD-3 than without the ligand. The NMR data also suggests that CRANAD-3 specifically interacts with the KLVFF core fragment. Based on fluorescence and NMR studies, an interaction model as shown in FIG. 5 is proposed, in which E-NH2 interacts with the boron-diketone motif, and VFF moiety forms hydrophobic interaction with pyridyl ring of CRANAD-3.

Example 6

Gel Electrophoresis and Western Blotting

Samples were separated on 4-20% gradient Tris-glycine mini gels (Invitrogen). For FAM-Aβ42 gels, the images were acquired on IVIS®Spectrum (Caliper, Perkin Elmer) with excitation=465 nm, and emission=520 nm. For native Aβ42 gels, the gel was transferred to a nitrocellulose membrane in a cooled transferring buffer and the membrane was blocked at room temperature for 2 hours. After blocking, the membrane was incubated in a solution of 6E10 anti-Aβ primary antibody (1:2000 dilution, Covance, Dedham, Mass.) at 4° C. overnight. After washing with TBS buffer, the membrane was incubated with the secondary antibody for 2 hours at room temperature. Western Breeze Chemiluminescent kit (Invitrogen) was used to visualize the bands. The images were acquired using IVIS®Spectrum (Caliper, Perkin Elmer) using bioluminescence imaging setting. SeeBlue®plus2 (Invitrogen)(4-250KD) was used as a molecular weight marker.

All the samples used for SDS-PAGE gel and Western blot were prepared using the same procedure as described below. A 5 µL HFIP (hexafluoroisopropanol) solution (25 µM) of native Aβ42 or FAM-Aβ42 was added to a 1.5 mL eppendorf tube. After evaporating the organic solvent under vacuum, a 5 µL at DMSO or DMSO solution of CRANAD-17 (100 µM) was added to the tube, followed by the addition of 15 µL of Vitamin C solution in PBS (33.3 µM) and 5 µL of copper sulfate solution in PBS (12.5 µM). The resulting mixture was incubated at 37° C. for 4 hours, and was then subjected to gel electrophoresis. For dose dependency study, 5 µL of DMSO solution of different CRANAD-17 concentrations (25, 125, 250 µM) was added to obtain CRANAD-17/Aβ42 ratio equals 1:1, 5:1, and 10:1.

Figure 6A:
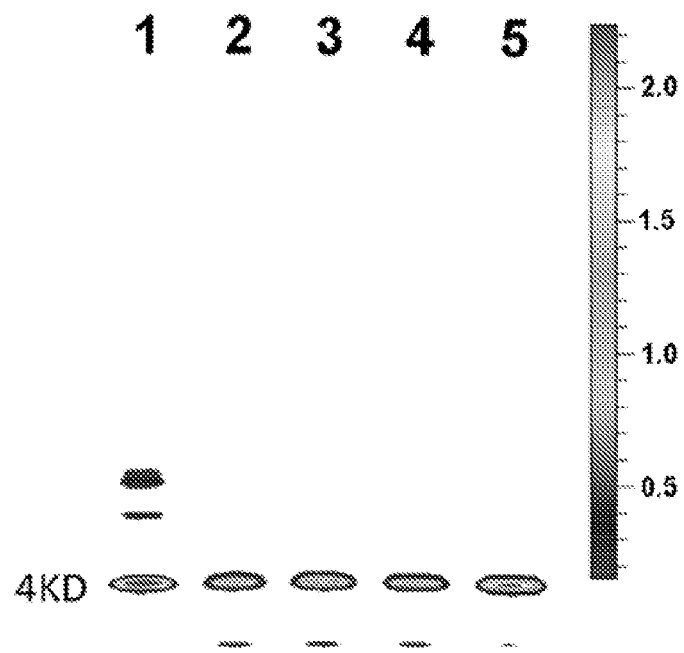
FIG. 6a shows an SDS-PAGE gel of FAM-Aβ42 alone (lane 1), CuSO$_4$ (lane 2), CuSO$_4$+curcumin (lane 3), CuSO$_4$+CRANAD-3 (lane 4), and CuSO$_4$+CRANAD-17 (lane 5)
Figure 6B:
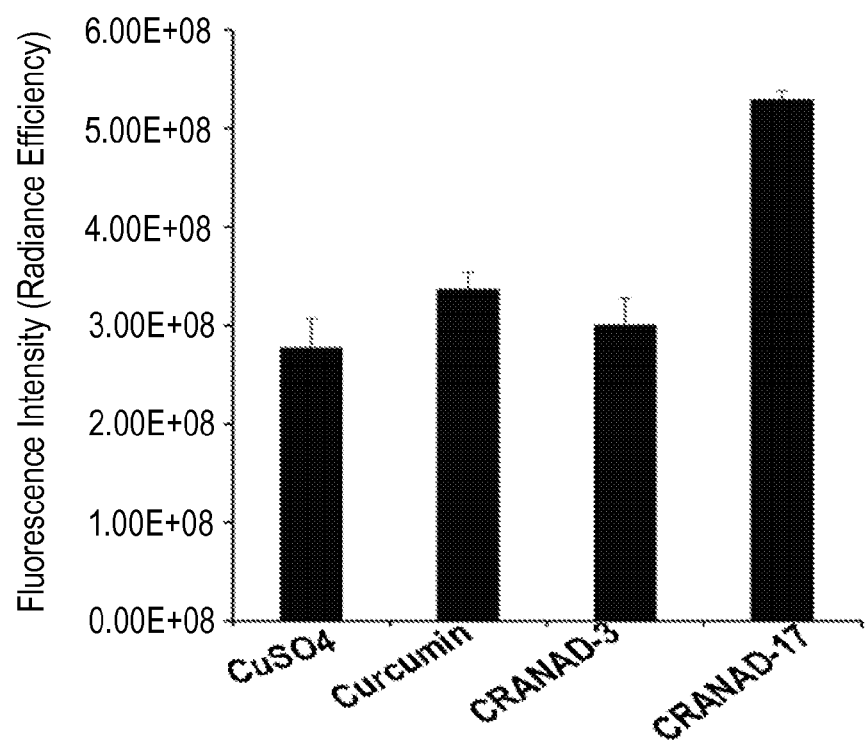
FIG. 6b is a quantitative analysis of the intensities of the monomeric bands in (FIG. 6a)

To investigate whether CRANAD-17 could attenuate copper-induced crosslinking of Aβ, a Aβ42 labeled with fluorescent dye (FAM) (FAM-Aβ42) was used as a model. Compared to traditional SDS-PAGE, the advantages of using dye-conjugated Aβ42 include easy and accurate detection using a fluorescence imaging system. To exclude the attenuation effect caused by the interaction of copper with the diketone moiety of curcumin, curcumin was used as a control compound. To compare the effect of the imidazolyl ring, CRANAD-3 was also used as a control compound. Due to numerous crosslinked products formed during natural or copper-induced crosslinking, quantification was based on the remaining amount of FAM-Aβ42 monomers (the starting material) on SDS-PAGE gel, which can be visualized with a fluorescence imaging system. It is known that covalent cross-linked Aβ species could not be dissociated by running SDS-PAGE gel, but other non-covalent aggregated species could be dissociated into monomers. Therefore, more crosslinking would result with fewer monomers, and less crosslinking would keep more monomers intact. After 4 hours of incubation of FAM-Aβ42 monomers with the compounds, copper sulfate, and vitamin C (used as an initiator), it was found that that the intensity of the monomeric Aβ bands with CRANAD-17, CRANAD-3, and curcumin were 1.92-, 1.21- and 1.07-fold higher than that of the non-treated group (FIG. 6a, b). These results indicated that CRANAD-17 had a significantly higher capacity for attenuating copper-induced crosslinking compared to curcumin and its analogues, primarily due to the interference and competition with copper coordination at the H13 position. Interestingly, no significant amount of high molecular weight oligomers or profibrils were found on the SDS-PAGE gel, this may be due to the fast aggregation of Aβ42 after copper treatment, which resulted in formation of insoluble species that could not enter into the gel.

Figure 6C:
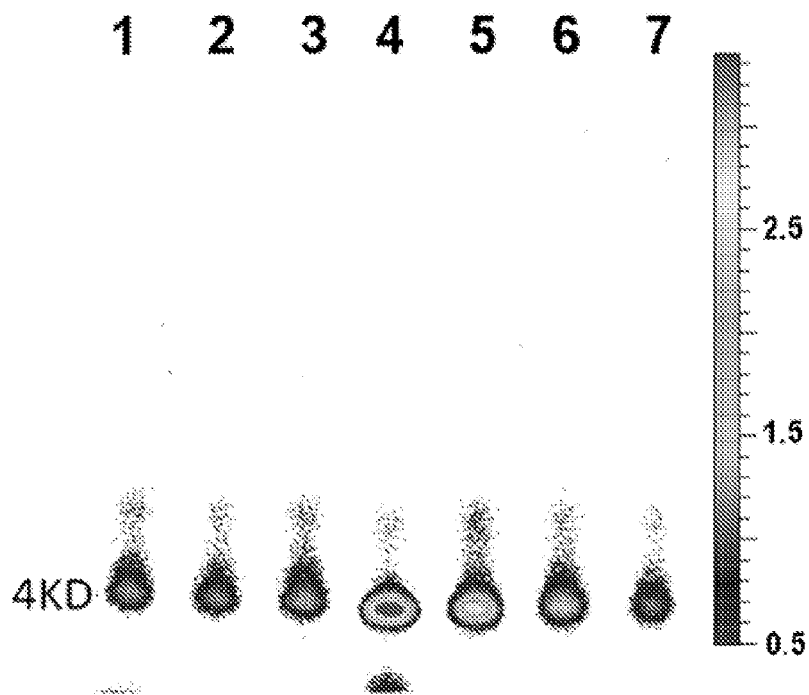
FIG. 6c is a picture representing the SDS-PAGE gel of FAM- Aβ42 treated with CuSO$_4$+imidazolium control (lane 1-3, ratio FAM- Aβ42/imidazolium 1:1, 1:5, 1:10), CuSO4+CRANAD-17 (lane 4-6, ratio FAM- Aβ42/CRANAD-17=1:10, 1:5, 1:1), and CuSO$_4$ only (lane 7)

In addition, it is possible that copper coordination with two imidazolium moieties from two CRANAD-17 molecules could lead to the lowering of copper concentration in solution, which thus results in less crosslinking To exclude this possibility, 4-(1H-imidazol-1-yl)benzene, which has an imidazolium ring for potential copper chelating, was used as a control compound. It was found that 4-(1H-imidazol-1-yl)benzene could indeed attenuate crosslinking, but the effect was relatively small compared to CRANAD-17 (FIG. 6c), suggesting that non-specific copper sequestration played only a minor role.

Figure 6D:
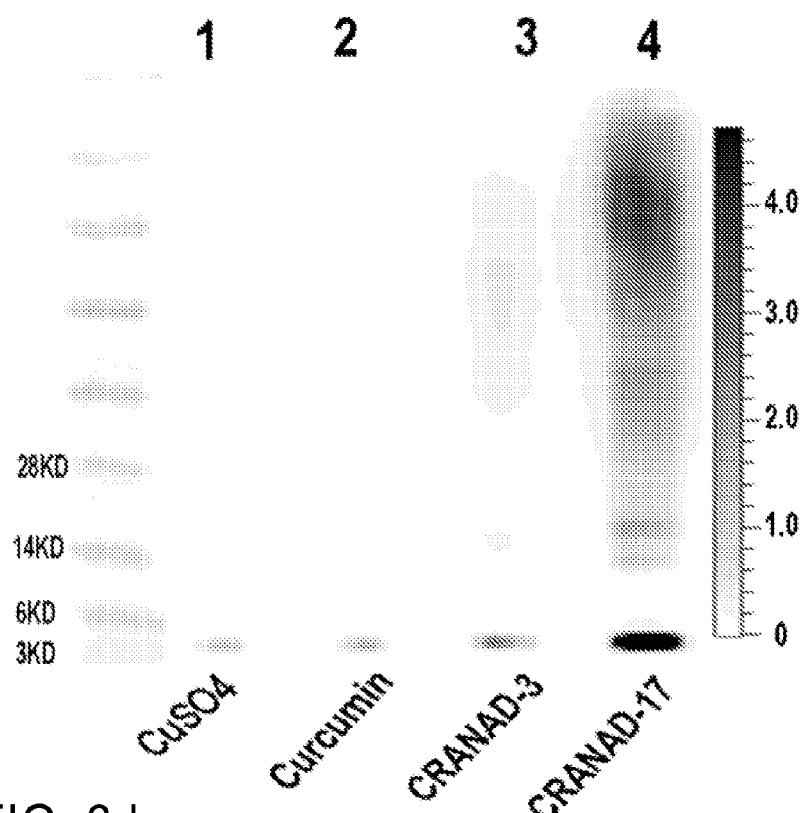
FIG. 6d provides a photograph of a Western blot of native Aβ42 with CuSO$_4$ (lane 1), CuSO$_4$+curcumin (lane 2), CuSO$_4$+CRANAD-3 (lane 3), and CuSO$_4$+CRANAD-17 (lane 4)
Figure 6E:
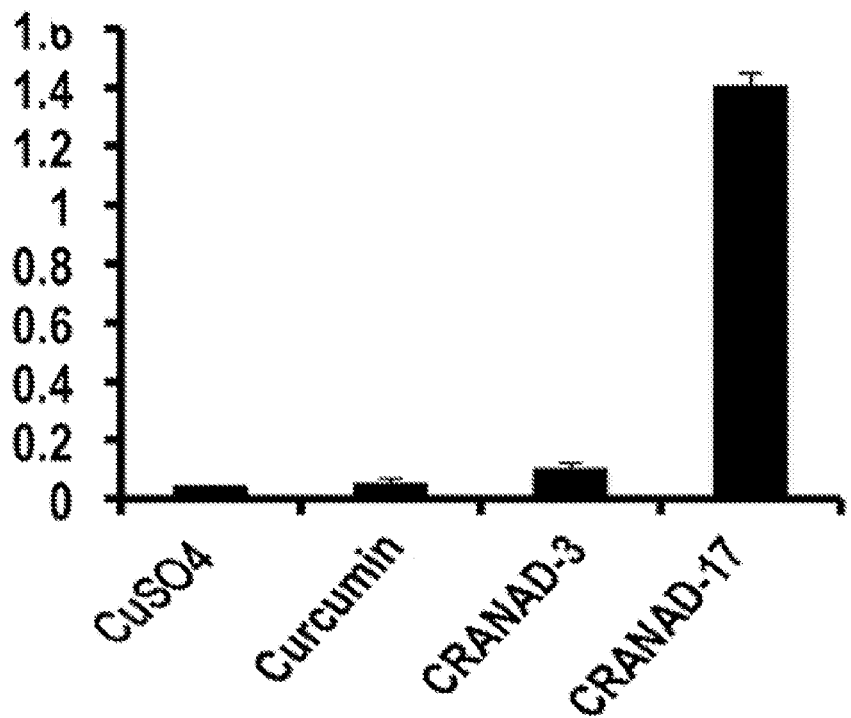
FIG. 6e is a bar graph showing the quantitative analysis of the monomeric bands in (FIG. 6d)
Figure 6F:
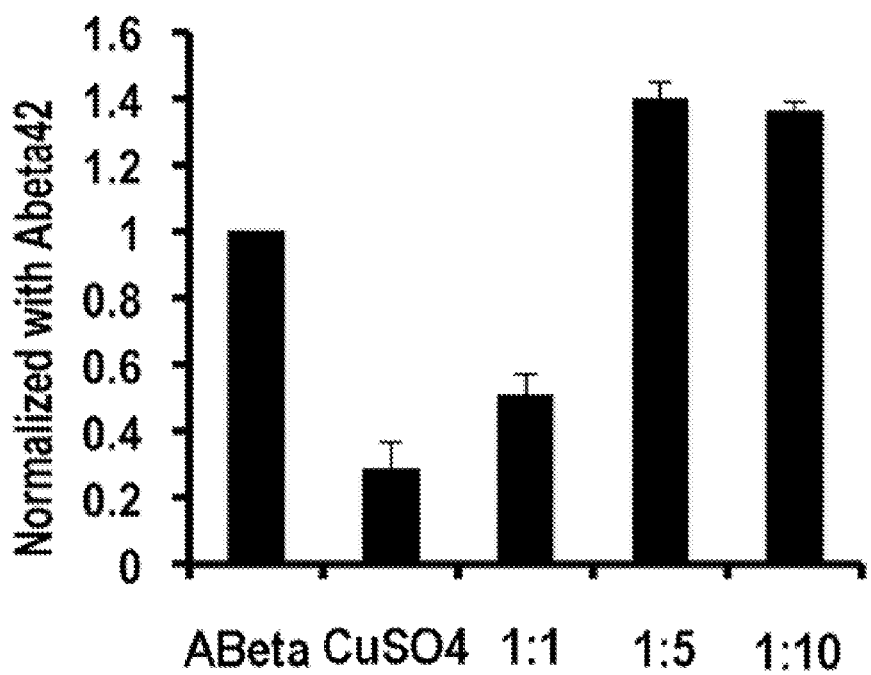
FIG. 6f is a bar graph illustrating the dose dependent study for CRANAD-17 with a quantitative analysis of the native Aβ42 monomeric bands (without copper), and with CuSO$_4$, and CuSO$_4$+CRANAD-17 (Aβ42/CRANAD-17=1:1, 1:5, and 1:10).

FAM-Aβ42 is an excellent model, however, it differs from its native Aβ counterpart in some aspects. Therefore, it was necessary to test whether the designed curcumin analogues were able to attenuate native Aβ crosslinking induced by copper. To this end, human Aβ42 was incubated with curcumin, CRANAD-3 and CRANAD-17 under the same conditions as above. Western blot results showed that curcumin, CRANAD-3 and CRANAD-17 could attenuate crosslinking (FIG. 6d,e). Similar to the results obtained with FAM-Aβ, CRANAD-17 showed a significantly higher attenuation effect than curcumin and CRANAD-3 (FIG. 6d,e), again suggesting that the imidazolium ring of CRANAD-17 played a primary role. It was also found that the attenuation effect of CRANAD-17 was concentration dependent (FIG. 6f), with the response reaching a plateau at a 5:1 CRANAD-17/Aβ42 ratio. Similar to the results obtained with FAM-Aβ42, no significant amount of high molecular weight species was observed for the groups treated with copper, copper+curcumin, and copper+CRANAD-3. These data most likely indicate that Aβ42 could aggregate quickly into insoluble species that are too large to enter the gel. It was observed that Aβ42 treated with CRANAD-17/copper showed a certain amount of high molecular weight oligomeric species (FIG. 6, lane4), suggesting that CRANAD-17 may slow down the aggregation process of Aβ42 induced by copper treatment.

Example 7

TEM Measurement and Thioflavin T Test

A 250 nM of Aβ42 in PBS solution was placed was at 37° C. for 24 hours. Next, 5 μL of this solution was dropped onto a Formvar coated TEM grid, followed by the addition of 2 μL of PTA contrast solution. After one minute, the liquid on the grid was carefully dried with a corner of a filter paper, and the resulting grid was further dried in the air for 2-5 minute. The TEM images were taken with JEOL 1011 electron microscope. Similar procedure was used for the incubated solution of CRANAD-l7 (1.0 μM) and Aβ42 (250 nM).

A 2.5 μM of Aβ42 solution in PBS was placed at 37° C. for 24 hours., and 10 μL of this solution was added to 1.0 ml PBS solution. The resulting solution was and then subjected to fluorescence spectrum recording with excitation=440 nm, and emission=470-800 nm (baseline recording). To this solution, 10 μL of thioflavin T (2.5 μM in PBS) was added and the spectrum was recorded. The quantification was conducted at λem=500 nm for Thioflavin T reading by subtracting the baseline reading. For CRANAD-17 (10 μM) incubation, the quantification was conducted by subtracting the readings at baseline and CRANAD-17 at λem=500 nm.

Figure 7B:
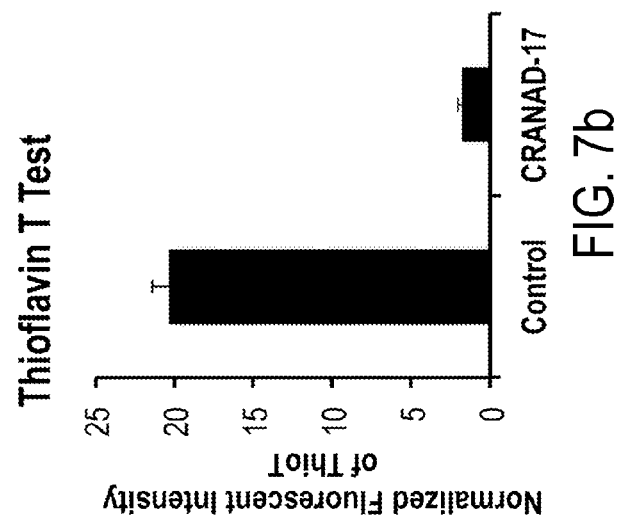
FIG. 7b shows the fluorescence intensity of Thioflavin T of solutions of Aβ42 treated with CuSO4 and CuSO4+CRANAD-17.
Figure 7A:
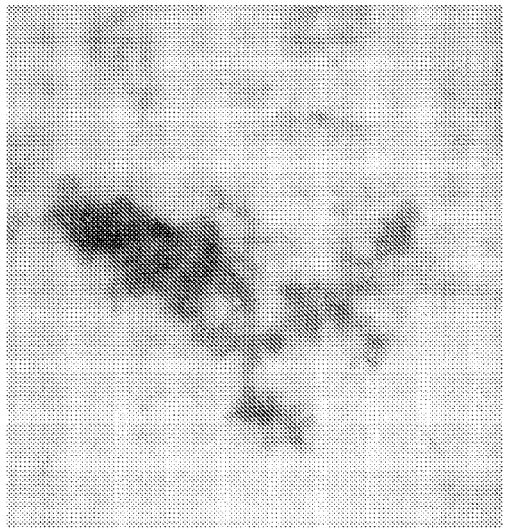
FIG. 7a is a TEM imaging of Aβ42 treated with CuSO4 (left), and with CuSO4+CRANAD-17 (right).
Figure 7A:
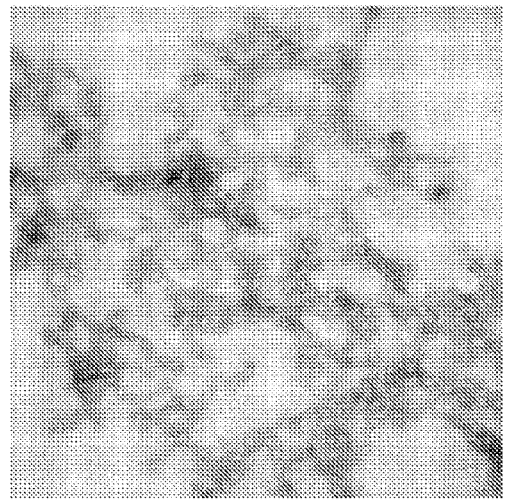
Figure 8A:
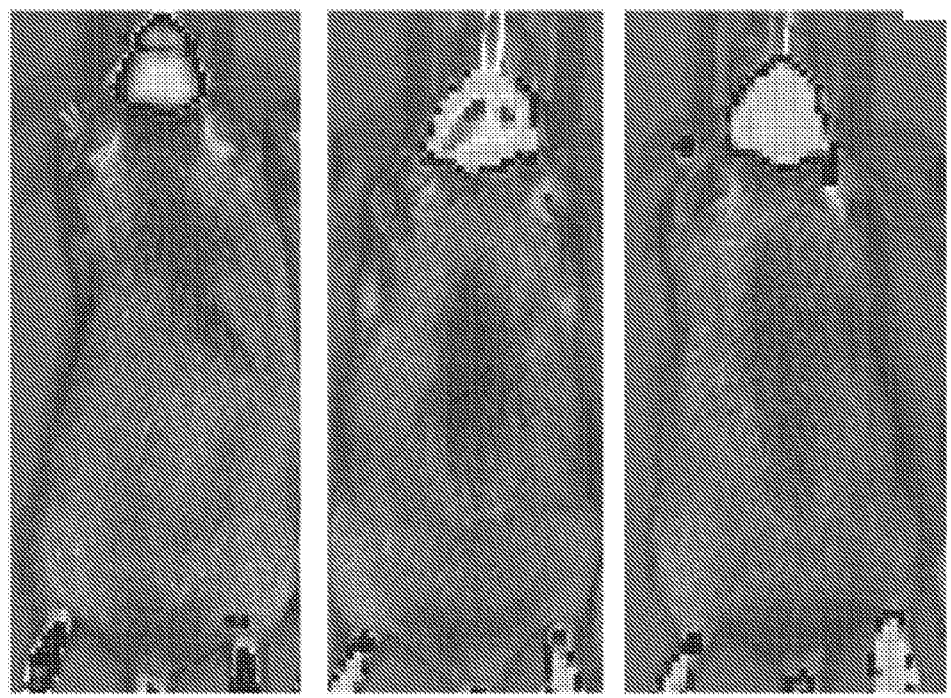
FIG. 8a is an in vivo image with CRANAD-3 after six-month treatment with CRANAD-17. Left: WT, middle: control, right: CRANAD-17.
Figure 8B:
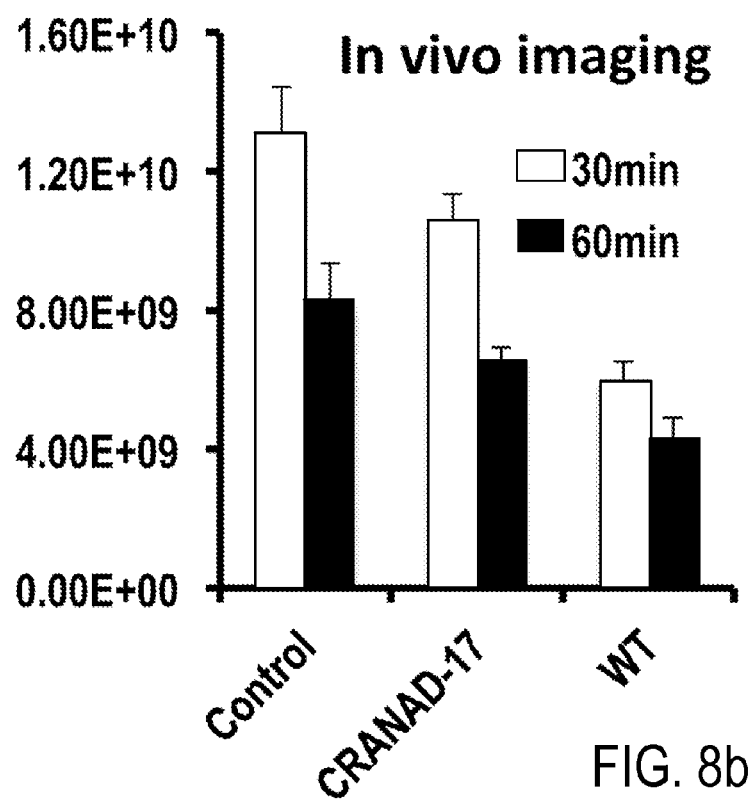
FIG. 8b shows the quantitative analysis of the images (n=5).
Figure 8C:
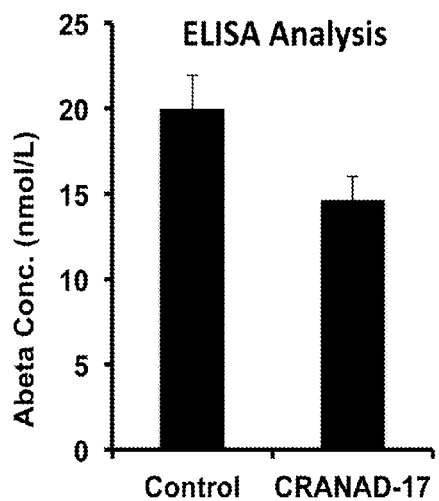
FIG. 8c provides the results of an ELISA for brain extraction.
Figure 8D:
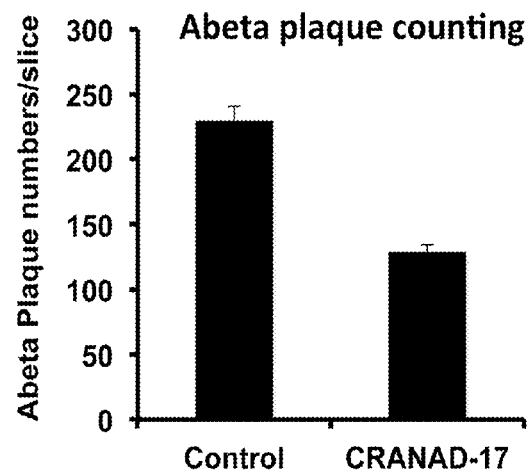
FIG. 8d is a bar graph showing the analysis of plaque counting.
Figure 8E:
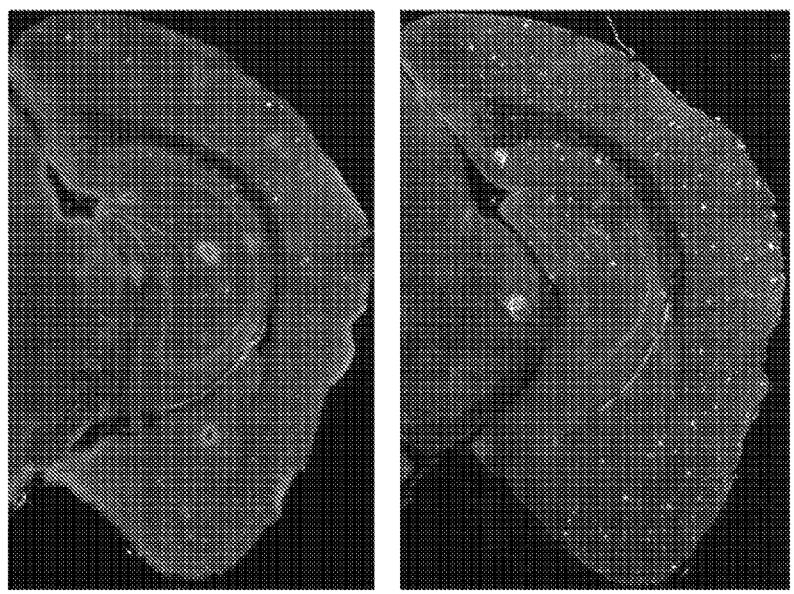
FIG. 8e is a representative histological staining with ThioT (Left: Control, Right: CRANAD-17).

To investigate whether CRANAD-17 was able to inhibit the aggregation of Aβ42 and to assess the degree of aggregation, both a TEM (transmission electron microscopy) and thioflavin T test was used. Compared to the control group (Aβ42 treated with copper only), we found less visible fibrils in CRANAD-17 treated group (FIG. 7a). Additionally, the thioflavin T test showed lower fluorescence signal after CRANAD-17 treatment (FIG. 7b), indicating that CRANAD-17 can also reduce Aβ42 aggregation.

Example 7

In Vivo Testing

Transgenic APP-PS1 mice and age-matched wild type mice were purchased from Jackson Laboratory. In vivo NIR imaging was recorded using the IVIS° Spectrum.

Ten APP/PS 1 mice (4-month) were divided into 2 groups (n=5/group), and one group was i.p. injected with 100 microliter of CRANAD-17 (4 mg/kg, formulated with10% cremophor, 10% DMSO and 80% PBS) twice a week. After 6-month treatment, the two groups were subjected to NIR imaging with CRANAD-3 (ex=605, em=680 nm), and then were sacrificed. The brain of each mouse was taken, and dissected in two halves. One half brain was subjected to extraction and then to ELISA analysis. The other half brain was dissected into 25 micron slices, and then the slices were stained with Thioflavin S. Eight slices from hippocampus area of each mouse were subjected to amyloid beta plaque counting by ImageJ.

As shown in FIG. 8 NIR imaging with CRANAD-3 indicated that CRANAD-17 treated group showed significant lower NIR signals (25%) than that of the non-treated group (a,b). This result is consistent with the ELISA analysis data (FIG. 2a; 36% reduction) for the brain extraction, and plaque counting (FIG. 2b,c; 78% reduction). All of the data indicates that CRANAD-17 could reduce amyloid beta content in the brain, and thus it has strong potential for therapeutic treatment.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A compound of Formula (I)

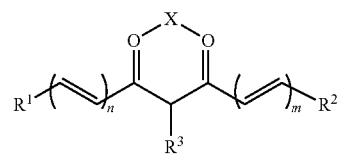

or a pharmaceutically acceptable salt thereof, wherein:
X is -BR$^4$R$^5$;
R$^1$ is an unsubstituted 5-membered N-containing heteroaryl or a 5-membered N-containing heteroaryl substituted by 1 or 2 groups independently selected from C$_{1-6}$ alkyl and C$_{6-10}$ aryl;

$R^2$ is an unsubstituted 5-membered N-containing heteroaryl or a 5-membered N-containing heteroaryl substituted by 1 or 2 groups independently selected from $C_{1-6}$ alkyl and $C_{6-10}$ aryl;

$R^3$ is H or a $(C_1-C_6)$alkyl;

$R^4$ and $R^5$ are independently selected from the group consisting of H, halo, and $OR^6$;

$R^6$ is H or a $(C_1-C_6)$alkyl; and n and m are each 1.

2. The compound of claim 1, wherein $R^4$ and $R^5$ are halo.

3. The compound of claim 2, wherein $R^4$ and $R^5$ are F.

4. The compound of claim 1, wherein $R^1$ and $R^2$ are the same.

5. The compound of claim 1, wherein the 5-membered N-containing heteroaryl is an imidazolyl.

6. The compound of claim 5, wherein the 5-membered N-containing heteroaryl is selected from the group consisting of:

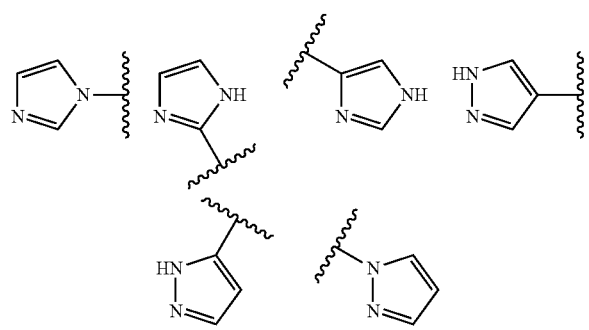

wherein each 5-membered N-containing heteroaryl is substituted by 1 or 2 substitutents indenpendently selected from $C_{1-6}$ alkyl and $C_{6-10}$ aryl, or unsubstituted.

7. A compound of Formula (II):

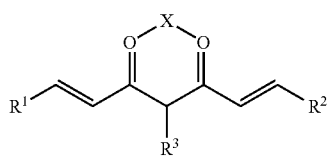

or a pharmaceutically acceptable salt thereof, wherein:

X —$BR^4R^5$, $R^1$ is an unsubstituted 5-membered N-containing heteroaryl or a 5-membered N-containing heteroaryl substituted by 1 or 2 groups independently selected from $C_{1-6}$ alkyl and $C_{6-10}$ aryl;

$R^2$ is an unsubstituted 5-membered N-containing heteroaryl or a 5-membered N-containing heteroaryl substituted by 1 or 2 groups independently selected from $C_{1-6}$ alkyl and $C_{6-10}$ aryl;

$R^3$ is H;

$R^4$ and $R^5$ are independently selected from the group consisting of H, halo, and $OR^6$;and $R^6$ is H or a $(C_1-C_6)$alkyl.

8. A compound of Formula (III)

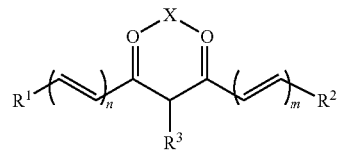

or a pharmaceutically acceptable salt thereof, wherein:

X is-$BR^4R^5$;

$R^1$ is an unsubstituted 5-membered N-containing heteroaryl or a 5-membered N-containing heteroaryl substituted by 1 or 2 groups independently selected from $C_{1-6}$ alkyl and $C_{6-10}$ aryl;

$R^2$ is an unsubstituted 5-membered N-containing heteroaryl or a 5-membered N-containing heteroaryl substituted by 1 or 2 groups independently selected from $C_{1-6}$ alkyl and $C_{6-10}$aryl;

$R^3$ is H or a $(C_1-C_6)$alkyl;

$R^4$ and $R^5$ are independently selected from the group consisting of H, halo, and $OR^6$;

$R^6$ is H or a $(C_1-C_6)$alkyl;

n and m are each 1; and wherein $R^1$ and $R^2$ are different.

9. A pharmaceutical composition comprising a compound of claim 1, or a pharmaceutically acceptable salt thereof, and a pharmaceutically acceptable excipient.

10. A method for treating Alzheimer's Disease in a patient, the method comprising administering to the patient a therapeutically effective amount of a compound of claim 1, or a pharmaceutically acceptable salt thereof.

11. The compound of claim 1, or a pharmaceutically acceptable salt thereof, wherein $R^1$ is a pyrazolyl ring substituted by 1 or 2 groups independently selected from $C_{1-6}$ alkyl and $C_{6-10}$ aryl.

12. The compound of claim 1, or a pharmaceutically acceptable salt thereof, wherein $R^2$ is a pyrazolyl ring substituted by 1 or 2 groups independently selected from $C_{1-6}$ alkyl and $C_{6-10}$ aryl.

13. The compound of claim 1, or a pharmaceutically acceptable salt thereof, wherein $R^1$ and $R^2$ are each a pyrazolyl ring substituted by 1 or 2 groups independently selected from $C_{1-6}$ alkyl and $C_{6-10}$ aryl.

14. The compound of claim 1, or a pharmaceutically acceptable salt thereof, wherein $R^1$ and $R^2$ are each a pyrazolyl ring substituted by methyl and phenyl.

15. The compound of claim 1, or a pharmaceutically acceptable salt thereof, wherein $R^1$ and $R^2$ are each 5-methyl-1-phenyl-1H-pyrazol-4-yl.

16. The compound of claim 1, or a pharmaceutically acceptable salt thereof, wherein:

X is -$BR^4R^5$;

$R^1$ and $R^2$ are each 5-methyl-1-phenyl-1H-pyrazol-4-yl;

$R^3$ is H;

$R^4$ and $R^5$ are each F; and n and m are each 1.

17. A compound selected from the group consisting of:

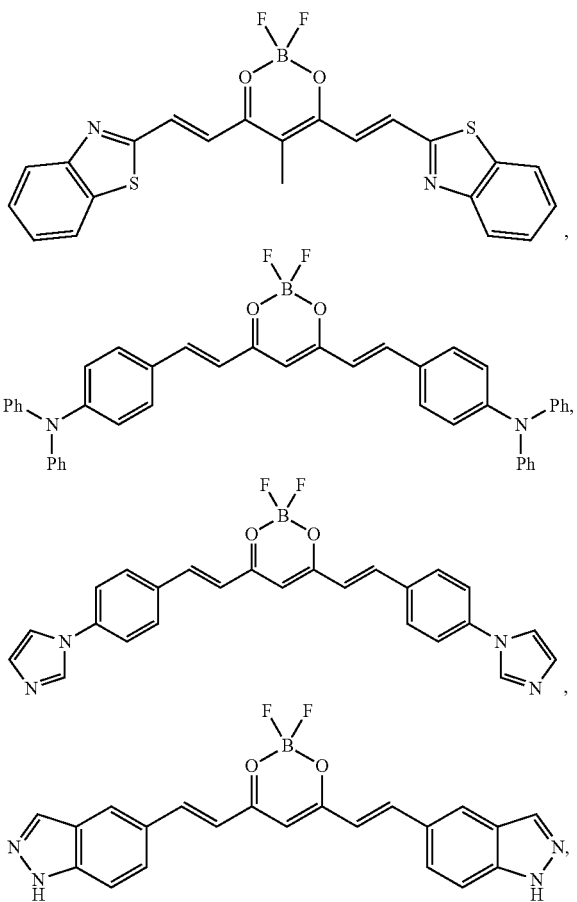

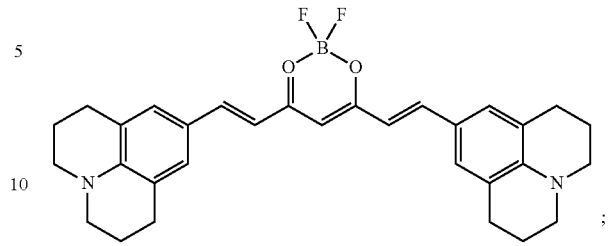

or a pharmaceutically acceptable salt thereof.

18. A method of inhibiting the crosslinking of amyloid beta in a cell, comprising contacting cell with a compound of claim 1, or a pharmaceutically acceptable salt thereof.

19. A method of inhibiting the crosslinking of amyloid beta in a cell, comprising contacting the cell with a compound of claim 16, or a pharmaceutically acceptable salt thereof.

20. A method of inhibiting the crosslinking of amyloid beta in a cell, comprising contacting the cell with a compound of claim 17, or a pharmaceutically acceptable salt thereof.

21. A method for treating Alzheimer's Disease in a patient, the method comprising administering to the patient a therapeutically effective amount of a compound of claim 16, or a pharmaceutically acceptable salt thereof.

22. A method for treating Alzheimer's Disease in a patient, the method comprising administering to the patient a therapeutically effective amount of a compound of claim 17, or a pharmaceutically acceptable salt thereof.

* * * * *